US011959088B2

(12) United States Patent
Michaud et al.

(10) Patent No.: US 11,959,088 B2
(45) Date of Patent: Apr. 16, 2024

(54) MODIFYING PROTEIN PRODUCTION IN PLANTS

(71) Applicants: MEDICAGO INC., Quebec (CA); UNIVERSITE LAVAL, Quebec (CA)

(72) Inventors: Dominique Michaud, Quebec (CA); Steeve Pepin, Quebec (CA); Gilbert Ethier, Morin-Heights (CA); Marie-Claire Goulet, Saint-Laurent-Ile-d'Orleans (CA); Linda Gaudreau, Saint-Laurent-Ile-d'Orleans (CA); Marielle Gagne, Chicoutimi (CA); Michele Martel, Quebec (CA); Nicole Bechtold, Quebec (CA); Marc-Andre D'Aoust, Quebec (CA); Andre Gosselin, Saint-Laurent-Ile-d'Orleans (CA)

(73) Assignees: ARAMIS BIOTECHNOLOGIES INC., Quebec (CA); UNIVERSITE LAVAL, Quebec (CA)

( * ) Notice: Subject to any disclaimer, the term of this patent is extended or adjusted under 35 U.S.C. 154(b) by 151 days.

(21) Appl. No.: 15/324,926

(22) PCT Filed: Jul. 10, 2015

(86) PCT No.: PCT/CA2015/050644
§ 371 (c)(1),
(2) Date: Jan. 9, 2017

(87) PCT Pub. No.: WO2016/004536
PCT Pub. Date: Jan. 14, 2016

(65) Prior Publication Data
US 2017/0204427 A1   Jul. 20, 2017

Related U.S. Application Data

(60) Provisional application No. 62/023,718, filed on Jul. 11, 2014.

(51) Int. Cl.
| C12N 15/82 | (2006.01) |
| A01H 3/00 | (2006.01) |
| A01H 3/02 | (2006.01) |
| A01H 3/04 | (2006.01) |

(52) U.S. Cl.
CPC .......... *C12N 15/8251* (2013.01); *A01H 3/00* (2013.01); *A01H 3/02* (2013.01); *A01H 3/04* (2013.01); *C12N 15/8258* (2013.01)

(58) Field of Classification Search
None
See application file for complete search history.

(56) References Cited

U.S. PATENT DOCUMENTS

| 4,326,877 A * | 4/1982 | Kazutoyo | C05F 11/00 504/241 |
| 4,945,050 A | 7/1990 | Sanford et al. | |
| 5,036,006 A | 7/1991 | Sanford et al. | |
| 5,100,792 A | 3/1992 | Sanford et al. | |
| 5,625,136 A | 4/1997 | Koziel et al. | |
| 6,245,717 B1 * | 6/2001 | Dean | A01N 37/10 504/321 |
| 6,403,865 B1 | 6/2002 | Koziel et al. | |
| 6,717,034 B2 * | 4/2004 | Jiang | C07K 14/415 800/290 |
| 8,674,084 B2 | 3/2014 | Sainsbury et al. | |
| 9,492,528 B2 * | 11/2016 | D'Aoust | A61K 39/145 |
| 2007/0287633 A1 * | 12/2007 | Herman | A01H 4/005 504/241 |
| 2012/0297507 A1 * | 11/2012 | Michoux | C12N 15/8214 800/298 |
| 2013/0130314 A1 * | 5/2013 | Williamson | C07K 14/005 435/69.1 |

FOREIGN PATENT DOCUMENTS

| CA | 1328236 | 4/1994 |
| EP | 0175966 A1 | 4/1986 |
| EP | 0290395 A2 | 11/1988 |
| EP | 0331083 A2 | 9/1989 |
| WO | 87/06614 A1 | 11/1987 |
| WO | 92/09696 A1 | 6/1992 |
| WO | 94/00583 A1 | 1/1994 |
| WO | 00/20557 A2 | 4/2000 |

(Continued)

OTHER PUBLICATIONS

Sugigura (J. Pestic. Sci., 2004, 29(4): 308-312).*
Jamal et al (Biotechnology Advances, 2009, 27: 914-923).*
Kato et al (Planta, 2004, 220(1): 97-104).*
Benedetto et al (The Americas Journal of Plant Science and Biotechnology, 2010, 4(1): 1-22).*
Clemente (2006, Nicotiana (Nicotiana tobaccum, Nicotiana benthamiana). In: Wang K. (eds) Agrobacterium Protocols. Methods in Molecular Biology, vol. 343. Humana Press.).*
De Lojo et al (Journal of Horticultural Science & Biotechnology, 2014, 89(2): 136-140).*
Stevens et al, 2000, Plant Physiology, 124: 173-182.*

(Continued)

*Primary Examiner* — Jason Deveau Rosen
(74) *Attorney, Agent, or Firm* — RAPHAEL BELLUM PLLC

(57) ABSTRACT

A method for synthesizing a protein of interest within a plant or a portion of a plant is provided. The method involves treating the plant to increase secondary leaf biomass production, followed by introducing one or more than one nucleic acid sequence encoding a protein of interest operatively linked with a regulatory region that is active in the plant, into the plant. The plant is then maintained under conditions that permit the nucleic acid sequence encoding the protein of interest to be expressed in the plant or the portion of the plant. Optionally, the plant or portion of the plant may be harvested and the protein of interest extracted.

18 Claims, 14 Drawing Sheets

Specification includes a Sequence Listing.

(56) References Cited

FOREIGN PATENT DOCUMENTS

| WO | 00/37663 A2 | 6/2000 |
| --- | --- | --- |
| WO | 00/63400 A2 | 10/2000 |
| WO | 01/94602 A2 | 12/2001 |
| WO | 2007/016276 A2 | 2/2007 |
| WO | 2007/135480 A1 | 11/2007 |
| WO | 2008/151440 A1 | 12/2008 |
| WO | 2008/151444 A1 | 12/2008 |
| WO | 2009/087391 A1 | 7/2009 |
| WO | 2010/025285 A1 | 3/2010 |
| WO | 2012/098119 A2 | 7/2012 |

OTHER PUBLICATIONS

Fujiuchi et al, 2014, Plant Biotechnology, 31:207-211 with a public availability date of May 27, 2014.*
Xie et al, 2003/2004, Tobacco Science, 46:17-23.*
Bilang et al., "The 3'-terminal region of the hygromycin-B-resistance gene is important for its activity in *Escherichia coli* and *Nicotiana tabacum*," Gene (1991) 100:247-250.
D'Aoust et al., "Influenza virus-like particles produced by transient expression in Nicotiana benthamiana induce a protective immune response against a lethal viral challenge in mice," Plant Biotechnology Journal (2008) 6:930-940.
D'Aoust et al., "Transient Expression of Antibodies in Plants Using Syringe Agroinfiltration," Methods in Molecular Biology, Recombinant Proteins From Plants, Humana Press Inc., Totowa, N.J., Ch. 3 (2009) 483:41-50.
De Block et al., "Transformation of *Brassica napus* and *Brassica oleracea* using Agrobacterium tumefaciens and the Expression of the bar and neo Genes in the Transgenic Plants," Plant Physiol. (1989) 91:694-701.
Freeman et al., "A Comparison of Methods for Plasmid Delivery into Plant Protoplasts," Plant Cell Physiol. (1984) 25(8):1353-1365.
Guerche et al., "Direct gene transfer by electroporation in Brassica napus," Plant Science (1987) 52:111-116.
Guerineau et al., "Plant transformation and expression vectors," in: Plant Molecular Biology Labfax (Croy RRD ed) Oxford, BIOS Scientific Publishers (1993) pp. 121-147.
Halfhill et al., "Spatial and temporal patterns of green fluorescent protein (GFP) fluorescence during leaf canopy development in transgenic oilseed rape, *Brassica napus* L.," Plant Cell Rep (2003) 22(5):338-343.
Hammatt et al., "Regeneration in Legumes," in: Cell Culture and Somatic Cell Genetics of Plants, vol. 3, Ch. 3, Academic Press, Inc., Editor Indra K. Vasil (1986) pp. 67-95.
Horsch et al., "A Simple and General Method for Transferring Genes into Plants," Science (1985) 227(4691):1229-1231.
Howell et al., "Cloned Cauliflower Mosaic Virus DNA Infects Turnips (*Brassica rapa*)," Science (1980) 208(4449):1265-1267.
Huang et al., "A DNA Replicon System for Rapid High-Level Production of Virus-Like Particles in Plants," Biotechnolo. Bioeng. (2009) 103(4):706-714.
Huang et al., "High-Level Rapid Production of Full-Size Monoclonal Antibodies in Plants by a Single-Vector DNA Replicon System," Biotechnol. Bioeng. (2010) 106(1):9-17.
Kapila et al., "An Agrobacterium-mediated transient gene expression system for intact leaves," Plant Science (1997) 122(1):101-108.
Klein et al., "High-velocity microprojectiles for delivering nucleic acids into living cells," Nature (1987) 327:70-73.
Liu et al., "Agroinfection as a rapid method for propagating Cowpea mosaic virus-based constructs," Journal of Virological Methods (2002) 105:343-348.
Miki et al., "Fundamentals of gene transfer in plants," in: Plant Metabolism, 2nd Ed. D.T. Dennis, D.H. Turpin, D.D. Lefebrve, D.B. Layzell (eds), Addison Wesley Longman Ltd. London (1997) pp. 561-579.
Neuhaus et al., "Transgenic rapeseed plants obtained by the microinjection of DNA into microspore-derived embryoids," Theor. Appl Genet. (1987) 75:30-36.
Ranch et al., "Plant Regeneration from Tissue Culture of Soybean by Somatic Embryogenesis," in: Cell Culture and Somatic Cell Genetics of Plants, vol. 3, Ch. 4, Academic Press, Inc., Editor Indra K. Vasil (1986) pp. 97-110.
Reynolds, "Regeneration in Vegetable Species," in: Cell Culture and Somatic Cell Genetics of Plants, vol. 3, Ch. 7, Academic Press, Inc., Editor Indra K. Vasil (1986) pp. 151-178.
Robert et al., "Protection of Recombinant Mammalian Antibodies from Development-Dependent Proteolysis in Leaves of Nicotiana benthamiana," PLOS One (2013) 8(7)e70203:1-9.
Sainsbury et al., "Expression of multiple proteins using full-length and deleted versions of cowpea mosaic virus RNA-2," Plant Biotechnology Journal (2008) 6:82-92.
Sainsbury et al., "Extremely High-Level and Rapid Transient Protein Production in Plants without the Use of Viral Replication," Plant Physiology (2008) 148:1212-1218.
Sainsbury et al., "pEAQ: versatile expression vectors for easy and quick transient expression of heterologous proteins in plants," Plant Biotechnology Journal (2009) 7:682-693.
Sainsbury et al., "Copea Mosaic Virus-Based Systems for the Expression of Antigens and Antibodies in Plants," in: Methods in Molecular Biology, Recombinant Proteins From Plants, Humana Press Inc., Totowa, N.J., Ch. 2 (2009) 483:25-39.
Scheid et al., "Reversible inactivation of a transgene in *Arabidopsis thaliana*," Mol. Gen. Genet. (1991) 228:104-112.
Spokevicius et al., "Agrobacterium-mediated transformation of dormant lateral buds in poplar trees reveals developmental patterns in secondary stem tissues," Functional Plant Biology (2006) 33:133-139.
Vasil et al., "Regeneration in Cereal and Other Grass Species," in: Cell Culture and Sometic Cell Genetics of Plants, vol. 3, Ch. 6, Academic Press, Inc., Editor Indra K. Vasil (1986) pp. 121-150.
Rogers et al., "Gene Transfer in Plants: Production of Transformed Plants Using Ti Plasmid Vectors," in: Methods for Plant Molecular Biology, Ch. 26, Academic Press, Inc., Editors Weissbach et al. (1988) pp. 423-463.
Wright et al., "Plant Regeneration from Tissue Culture of Soybean by Organogenesis," in: Cell Culture and Somatic Cell Genetics of Plants, vol. 3, Ch. 5, Academic Press, Inc., Editor Indra K. Vasil (1986) pp. 111-119.
Wydro et al., "Optimization of transient Agrobacterium-mediated gene expression system in leaves of Nicotiana benthamiana," Acta Biochimica Polonica (2006) 53(2):289-298.
Zhang et al., "Bean Yellow Dwarf Virus Replicons for High-Level Transgene Expression in Transgenic Plants and Cell Cultures," Biotechnolo. Bioeng. (2006) 93(2):271-279.
Nam et al., "The Effect of BAP on the Gene Expression of a Small GTP-Binding Protein, Rho1Ps in a Shoot Apex of Garden Pea," J. Plant Biol. (1998) 41(1):64-67.
International Search Report and Written Opinion in International Application No. PCT/CA2015/050644, dated Oct. 19, 2015.
Extended European Search Report in Application No. 15819391.2, dated Nov. 10, 2017.
Goulet et al., "Production of Biopharmaceuticals in Nicotiana Benthamiana—Axillary Stem Growth as A Key Determinant of Total Protein Yield," Frontiers in Plant Science, 10, 2019, 1-9.

* cited by examiner

Figure 12: A-2X35S/CPMV-HT/ PDISP/H3 Victoria/ NOS (Construct number 1391)

Figure 12A, IF-PDI.S1+3c; SEQ ID NO: 1

AAATTTGTCGGGCCCATGGCGAAAAACGTTGCGATTTTCGGCTTATTG

Figure 12B, IF-H1cTMCT.S1-4r; SEQ ID NO: 2

ACTAAAGAAAATAGGCCTTTAAATACATATTCTACACTGTAGAGAC

Figure 13, Nucleotide sequence of PDISP/H1 California; SEQ ID NO :3

```
ATGGCGAAAAACGTTGCGATTTTCGGCTTATTGTTTTCTCTTCTTGTGTTGGTTCCTTCTCAGATCTTCGCTGACAC
ATTATGTATAGGTTATCATGCGAACAATTCAACAGACACTGTAGACACAGTACTAGAAAAGAATGTAACAGTAACAC
ACTCTGTTAACCTTCTAGAAGACAAGCATAACGGGAAACTATGCAAACTAAGAGGGGTAGCCCCATTGCATTTGGGT
AAATGTAACATTGCTGGCTGGATCCTGGGAAATCCAGAGTGTGAATCACTCTCCACAGCAAGCTCATGGTCCTACAT
TGTGGAAACACCTAGTTCAGACAATGGAACGTGTTACCCAGGAGATTTCATCGATTATGAGGAGCTAAGAGAGCAAT
TGAGCTCAGTGTCATCATTTGAAAGGTTTGAGATATTCCCCAAGACAAGTTCATGGCCCAATCATGACTCGAACAAA
GGTGTAACGGCAGCATGTCCTCATGCTGGAGCAAAAAGCTTCTACAAAAATTTAATATGGCTAGTTAAAAAAGGAAA
TTCATACCCAAAGCTCAGCAAATCCTACATTAATGATAAAGGGAAAGAAGTCCTCGTGCTATGGGGCATTCACCATC
CATCTACTAGTGCTGACCAACAAAGTCTCTATCAGAATGCAGATGCATATGTTTTTGTGGGGTCATCAAGATACAGC
AAGAAGTTCAAGCCGGAAATAGCAATAAGACCCAAAGTGAGGGATCAAGAAGGGAGAATGAACTATTACTGGACACT
AGTAGAGCCGGGAGACAAAATAACATTCGAAGCAACTGGAAATCTAGTGGTACCGAGATATGCATTCGCAATGGAAA
GAAATGCTGGATCTGGTATTATCATTTCAGATACACCAGTCCACGATTGCAATACAACTTGTCAAACACCCAAGGGT
GCTATAAACACCAGCCTCCCATTTCAGAATATACATCGATCACAATTGGAAAATGTCCAAAATATGTAAAAAGCAC
AAAATTGAGACTGGCCACAGGATTGAGGAATATCCCGTCTATTCAATCTAGAGGACTATTTGGGGCCATTGCCGGTT
TCATTGAAGGGGGGTGGACAGGGATGGTAGATGGATGGTACGGTTATCACCATCAAAATGAGCAGGGGTCAGGATAT
GCAGCCGACCTGAAGAGCACACAGAATGCCATTGACGAGATTACTAACAAAGTAAATTCTGTTATTGAAAGATGAA
TACACAGTTCACAGCAGTAGGTAAAGAGTTCAACCACCTGGAAAAAAGAATAGAGAATTTAAATAAAAAAGTTGATG
ATGGTTTCCTGGACATTTGGACTTACAATGCCGAACTGTTGGTTCTATTGGAAAATGAAAGAACTTTGGACTACCAC
GATTCAAATGTGAAGAACTTATATGAAAAGGTAAGAAGCCAGCTAAAAAACAATGCCAAGGAAATTGGAAACGGCTG
CTTTGAATTTTACCACAAATGCGATAACACGTGCATGGAAAGTGTCAAAAATGGGACTTATGACTACCCAAAATACT
CAGAGGAAGCAAAATTAAACAGAGAAGAAATAGATGGGGTAAAGCTGGAATCAACAAGGATTTACCAGATTTTGGCG
ATCTATTCAACTGTCGCCAGTTCATTGGTACTGGTAGTCTCCCTGGGGCAATCAGTTTCTGGATGTGCTCTAATGG
GTCTCTACAGTGTAGAATATGTATTTAA
```

Figure 14, Schematic representation of construct 1191. SacII and StuI restriction enzyme sites used for plasmid linearization are annotated on the representation.
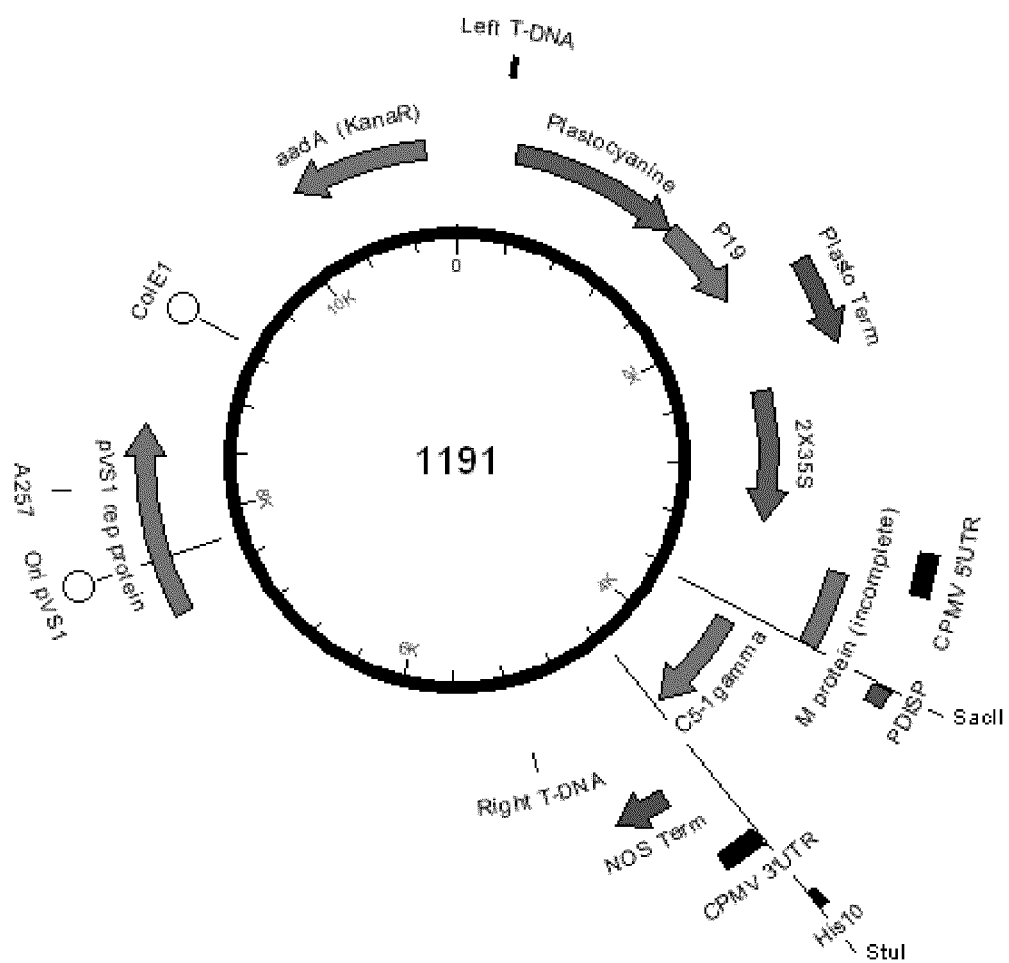

Figure 15, SEQ ID NO: 4 Construct 1191 from left to right t-DNA borders (underlined). 2X35S/CPMV-HT/NOS with Plastocyanine-P19-Plastocyanine silencing inhibitor expression cassette

```
TGGCAGGATATATTGTGGTGTAAACAAATTGACGCTTAGACAACTTAATAACACATTGCGGACGTTTTTAATGTACT
GAATTAACGCCGAATCCCGGGCTGGTATATTTATATGTTGTCAAATAACTCAAAAACCATAAAAGTTTAAGTTAGCA
AGTGTGTACATTTTTACTTGAACAAAAATATTCACCTACTACTGTTATAAATCATTATTAAACATTAGAGTAAAGAA
ATATGGATGATAAGAACAAGAGTAGTGATATTTTGACAACAATTTTGTTGCAACATTTGAGAAAATTTTGTTGTTCT
CTCTTTTCATTGGTCAAAAACAATAGAGAGAGAAAAAGGAAGAGGGAGAATAAAAACATAATGTGAGTATGAGAGAG
AAAGTTGTACAAAAGTTGTACCAAAATAGTTGTACAAATATCATTGAGGAATTTGACAAAAGCTACACAAATAAGGG
TTAATTGCTGTAAATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAATTGATGAAAGA
GTTGGATTAAAGTTGTATTAGTAATTAGAATTTGGTGTCAAATTTAATTTGACATTTGATCTTTTCCTATATATTGC
CCCATAGAGTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGATAACATCCA
ATCCAACCAATCACAACAATCCTGATGAGATAACCCACTTTAAGCCCACGCATCTGTGGCACATCTACATTATCTAA
ATCACACATTCTTCCACACATCTGAGCCACACAAAAACCAATCCACATCTTTATCACCCATTCTATAAAAAATCACA
CTTTGTGAGTCTACACTTTGATTCCCTTCAAACACATACAAAGAGAAGAGACTAATTAATTAATTAATCATCTTGAG
AGAAAATGGAACGAGCTATACAAGGAAACGACGCTAGGGAACAAGCTAACAGTGAACGTTGGGATGGAGGATCAGGA
GGTACCACTTCTCCCTTCAAACTTCCTGACGAAAGTCCGAGTTGGACTGAGTGGCGGCTACATAACGATGAGACGAA
TTCGAATCAAGATAATCCCCTTGGTTTCAAGGAAAGCTGGGGTTTCGGGAAAGTTGTATTTAAGAGATATCTCAGAT
ACGACAGGACGGAAGCTTCACTGCACAGAGTCCTTGGATCTTGGACGGGAGATTCGGTTAACTATGCAGCATCTCGA
TTTTTCGGTTTCGACCAGATCGGATGTACCTATAGTATTCGGTTTCGAGGAGTTAGTATCACCGTTTCGGAGGGTC
GCGAACTCTTCAGCATCTCTGTGAGATGGCAATTCGGTCTAAGCAAGAACTGCTACAGCTTGCCCCAATCGAAGTGG
AAAGTAATGTATCAAGAGGATGCCCTGAAGGTACTCAAACCTTCGAAAAAGAAAGCGAGTAAGTTAAAATGCTTCTT
CGTCTCCTATTTATAATATGGTTTGTTATTGTTAATTTTGTTCTTGTAGAAGAGCTTAATTAATCGTTGTTGTTATG
AAATACTATTTGTATGAGATGAACTGGTGTAATGTAATTCATTTACATAAGTGGAGTCAGAATCAGAATGTTTCCTC
CATAACTAACTAGACATGAAGACCTGCCGCGTACAATTGTCTTATATTTGAACAACTAAAATTGAACATCTTTTGCC
ACAACTTTATAAGTGGTTAATATAGCTCAAATATATGGTCAAGTTCAATAGATTAATAATGGAAATATCAGTTATCG
AAATTCATTAACAATCAACTTAACGTTATTAACTACTAATTTTATATCATCCCCTTTGATAAATGATAGTACACCAA
TTAGGAAGGAGCATGCTCGCCTAGGAGATTGTCGTTTCCCGCCTTCAGTTTGCAAGCTGCTCTAGCCGTGTAGCCAA
TACGCAAACCGCCTCTCCCCGCGCGTTGGGAATTACTAGCGCGTGTCGACAAGCTTGCATGCCGGTCAACATGGTGG
AGCACGACACACTTGTCTACTCCAAAAATATCAAAGATACAGTCTCAGAAGACCAAAGGGCAATTGAGACTTTTCAA
CAAAGGGTAATATCCGGAAACCTCCTCGGATTCCATTGCCCAGCTATCTGTCACTTTATTGTGAAGATAGTGGAAAA
GGAAGGTGGCTCCTACAAATGCCATCATTGCGATAAAGGAAAGGCCATCGTTGAAGATGCCTCTGCCGACAGTGGTC
CCAAAGATGGACCCCCACCCACGAGGAGCATCGTGGAAAAAGAAGACGTTCCAACCACGTCTTCAAAGCAAGTGGAT
TGATGTGATAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTCACTTTA
TTGTGAAGATAGTGGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAGACGTTCCAACCAC
GTCTTCAAAGCAAGTGGATTGATGTGATATCTCCACTGACGTAAGGGATGACGCACAATCCCACTATCCTTCGCAAG
ACCCTTCCTCTATATAAGGAAGTTCATTTCATTTGGAGAGGTATTAAAATCTTAATAGGTTTTGATAAAAGCGAACG
TGGGGAAACCCGAACCAAACCTTCTTCTAAACTCTCTCTCATCTCTCTTAAAGCAAACTTCTCTCTTGTCTTTCTTG
CGTGAGCGATCTTCAACGTTGTCAGATCGTGCTTCGGCACCAGTACAACGTTTCTTTCACTGAAGCGAAATCAAAG
ATCTCTTTGTGGACACGTAGTGCGGCGCCATTAAATAACGTGTACTTGTCCTATTCTTGCGGTGTGGTCTTGGGAA
AAGAAAGCTTGCTGGAGGCTGCTGTTCAGCCCATACATTACTTGTTACGATTCTGCTGACTTTCGGCGGGTGCAAT
ATCTCTACTTCTGCTTGACGAGGTATTGTTGCCTGTACTTCTTTCTTCTTCTTGCTGATTGGTTCTATAAGAAA
TCTAGTATTTTCTTTGAAACAGAGTTTTCCCGTGGTTTTCGAACTTGGAGAAAGATTGTTAAGCTTCTGTATATTCT
GCCCAAATTTGTCGGGCCCGCGGATGGCGAAAAACGTTGCGATTTTCGGCTTATTGTTTTCTCTTCTTGTGTTGGTT
CCTTCTCAGATCTTCGCCTGCAGGCTCCTCAGCCAAAACGACACCCCATCGTCTATCCACTGGCCCCTGGATCTG
CTGCCCAAACTAACTCCATGGTGACCCTGGGATGCCTGGTCAAGGGCTATTTCCCTGAGCCAGTGACAGTGACCTGG
AACTCTGGATCCCTGTCCAGCGGTGTGCACACCTTCCCAGCTGTCCTGCAGTCTGACCTCTACACTCTGAGCAGCTC
AGTGACTGTCCCCTCCAGCACCTGGCCCAGCGAGACCGTCACCTGCAACGTTGCCCACCCGGCCAGCAGCACCAAGG
TGGACAAGAAAATTGTGCCCAGGGATTGTGGTTGTAAGCCTTGCATATGTACAGTCCCAGAAGTATCATCTGTCTTC
ATCTTCCCCCCAAAGCCCAAGGATGTGCTCACCATTACTCTGACTCCTAAGGTCACGTGTGTTGTGGTAGACATCAG
CAAGGATGATCCCGAGGTCCAGTTCAGCTGGTTTGTAGATGATGTGGAGGTGCACACAGCTCAGACGCAACCCCGGG
```

Figure 15 cont

```
AGGAGCAGTTCAACAGCACTTTCCGCTCAGTCAGTGAACTTCCCATCATGCACCAGGACTGGCTCAATGGCAAGGAG
CGATCGCTCACCATCACCATCACCATCACCATCACCATTAAAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATTTAATTTCTTTGTG
AGCTCCTGTTTAGCAGGTCGTCCCTTCAGCAAGGACACAAAAAGATTTTAATTTTATTAAAAAAAAAAAAAAAAAAG
ACCGGGAATTCGATATCAAGCTTATCGACCTGCAGATCGTTCAAACATTTGGCAATAAAGTTTCTTAAGATTGAATC
CTGTTGCCGGTCTTGCGATGATTATCATATAATTTCTGTTGAATTACGTTAAGCATGTAATAATTAACATGTAATGC
ATGACGTTATTTATGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGATCTCTAGAGTCTCAAGCTTGGCG
CGCCCACGTGACTAGTGGCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGATCGCCCTTCCCAACAGTT
GCGCAGCCTGAATGGCGAATGCTAGAGCAGCTTGAGCTTGGATCAGATTGTCGTTTCCCGCCTTCAGTTTAAACTAT
CAGTGTTTGACAGGATATATTGGCGGGTAAACCTAAGAGAAAAGAGCGTTTA
```

Figure 16, SEQ ID NO: 5

Expression cassette number 484 from 2X35S promoter to NOS terminator. PDISP/H1 California nucleotide sequence is underlined.

```
GTCAACATGGTGGAGCACGACACACTTGTCTACTCCAAAAATATCAAAGATACAGTCTCAGAAGACCAAAGGGCAAT
TGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTCT
GCCGACAGTGGTCCCAAAGATGGACCCCCACCCACGAGGAGCATCGTGGAAAAAGAAGACGTTCCAACCACGTCTTC
AAAGCAAGTGGATTGATGTGATAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGCCCAGCT
ATCTGTCACTTTATTGTGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCGTGGAAAAAGAAG
ACGTTCCAACCACGTCTTCAAAGCAAGTGGATTGATGTGATATCTCCACTGACGTAAGGGATGACGCACAATCCCAC
TATCCTTCGCAAGACCCTTCCTCTATATAAGGAAGTTCATTTCATTTGGAGAGGTATTAAAATCTTAATAGGTTTTG
ATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAACGTTTTCTTTCACTGA
AGCGAAATCAAAGATCTCTTTGTGGACACGTAGTGCGGCGCCATTAAATAACGTGTACTTGTCCTATTCTTGTCGGT
GTGGTCTTGGGAAAAGAAAGCTTGCTGGAGGCTGCTGTTCAGCCCCATACATTACTTGTTACGATTCTGCTGACTTT
CGGCGGGTGCAATATCTCTACTTCTGCTTGACGAGGTATTGTTGCCTGTACTTCTTTCTTCTTCTTCTTGCTGATTG
GTTCTATAAGAAATCTAGTATTTTCTTTGAAACAGAGTTTTCCCGTGGTTTTCGAACTTGGAGAAAGATTGTTAAGC
TTCTGTATATTCTGCCCAAATTTGTCGGGCCCATGGCGAAAAACGTTGCGATTTTCGGCTTATTGTTTTCTCTTCTT
GTGTTGGTTCCTTCTCAGATCTTCGCTGACACATTATGTATAGGTTATCATGCGAACAATTCAACAGACACTGTAGA
CACAGTACTAGAAAAGAATGTAACAGTAACACACTCTGTTAACCTTCTAGAAGACAAGCATAACGGGAAACTATGCA
AACTAAGAGGGGTAGCCCCATTGCATTTGGGTAAATGTAACATTGCTGGCTGGATCCTGGGAAATCCAGAGTGTGAA
TCACTCTCCACAGCAAGCTCATGGTCCTACATTGTGGAAACACCTAGTTCAGACAATGGAACGTGTTACCCAGGAGA
TTTCATCGATTATGAGGAGCTAAGAGAGCAATTGAGCTCAGTGTCATCATTTGAAAGGTTTGAGATATTCCCCAAGA
CAAGTTCATGGCCCAATCATGACTCGAACAAAGGTGTAACGGCAGCATGTCCTCATGCTGGAGCAAAAAGCTTCTAC
AAAAATTTAATATGGCTAGTTAAAAAAGGAAATTCATACCCAAAGCTCAGCAAATCCTACATTAATGATAAAGGGAA
AGAAGTCCTCGTGCTATGGGGCATTCACCATCCATCTACTAGTGCTGACCAACAAAGTCTCTATCAGAATGCAGATG
CATATGTTTTTGTGGGGTCATCAAGATACAGCAAGAAGTTCAAGCCGGAAATAGCAATAAGACCCAAAGTGAGGGAT
CAAGAAGGGAGAATGAACTATTACTGGACACTAGTAGAGCCGGGAGACAAAATAACATTCGAAGCAACTGGAAATCT
AGTGGTACCGAGATATGCATTCGCAATGGAAAGAAATGCTGGATCTGGTATTATCATTTCAGATACACCAGTCCACG
ATTGCAATACAACTTGTCAAACACCCAAGGGTGCTATAAACACCAGCCTCCCATTTCAGAATATACATCCGATCACA
ATTGGAAAATGTCCAAAATATGTAAAAAGCACAAAATTGAGACTGGCCACAGGATTGAGGAATATCCCGTCTATTCA
ATCTAGAGGACTATTTGGGGCCATTGCCGGTTTCATTGAAGGGGGGTGGACAGGGATGGTAGATGGATGGTACGGTT
ATCACCATCAAAATGAGCAGGGGTCAGGATATGCAGCCGACCTGAAGAGCACACAGAATGCCATTGACGAGATTACT
AACAAAGTAAATTCTGTTATTGAAAAGATGAATACACAGTTCACAGCAGTAGGTAAAGAGTTCAACCACCTGGAAAA
AAGAATAGAGAATTTAAATAAAAAAGTTGATGATGGTTTCCTGGACATTTGGACTTACAATGCCGAACTGTTGGTTC
TATTGGAAAATGAAAGAACTTTGGACTACCACGATTCAAATGTGAAGAACTTATATGAAAAGGTAAGAAGCCAGCTA
AAAAACAATGCCAAGGAAATTGGAAACGGCTGCTTTGAATTTTACCACAAATGCGATAACACGTGCATGGAAAGTGT
CAAAAATGGGACTTATGACTACCCAAAATACTCAGAGGAAGCAAAATTAAACAGAGAAGAAATAGATGGGGTAAAGC
TGGAATCAACAAGGATTTACCAGATTTTGGCGATCTATTCAACTGTCGCCAGTTCATTGGTACTGGTAGTCTCCCTG
GGGGCAATCAGTTTCTGGATGTGCTCTAATGGGTCTCTACAGTGTAGAATATGTATTTAAAGGCCTATTTCTTTAG
TTTGAATTTACTGTTATTCGGTGTGCATTTCTATGTTTGGTGAGCGGTTTTCTGTGCTCAGAGTGTGTTTATTTTAT
GTAATTTAATTTCTTTGTGAGCTCCTGTTTAGCAGGTCGTCCCTTCAGCAAGGACACAAAAAGATTTTAATTTTATT
AAAAAAAAAAAAAAAAAGACCGGAATTCGATATCAAGCTTATCGACCTGCAGATCGTTCAAACATTTGGCAATAA
AGTTTCTTAAGATTGAATCCTGTTGCCGGTCTTGCGATGATTATCATATAATTTCTGTTGAATTACGTTAAGCATGT
AATAATTAACATGTAATGCATGACGTTATTTATGAGATGGGTTTTTATGATTAGAGTCCCGCAATTATACATTTAAT
ACGCGATAGAAAACAAAATATAGCGCGCAAACTAGGATAAATTATCGCGCGCGGTGTCATCTATGTTACTAGAT
```

Figure 17, SEQ ID NO: 6

Amino acid sequence of PDISP/H1 California.

```
MAKNVAIFGLLFSLLVLVPSQIFADTLCIGYHANNSTDTVDTVLEKNVTVTHSVNLLEDKHNGKLCKLRGVAPLHLG
KCNIAGWILGNPECESLSTASSWSYIVETPSSDNGTCYPGDFIDYEELREQLSSVSSFERFEIFPKTSSWPNHDSNK
GVTAACPHAGAKSFYKNLIWLVKKGNSYPKLSKSYINDKGKEVLVLWGIHHPSTSADQQSLYQNADAYVFVGSSRYS
KKFKPEIAIRPKVRDQEGRMNYYWTLVEPGDKITFEATGNLVVPRYAFAMERNAGSGIIISDTPVHDCNTTCQTPKG
AINTSLPFQNIHPITIGKCPKYVKSTKLRLATGLRNIPSIQSRGLFGAIAGFIEGGWTGMVDGWYGYHHQNEQGSGY
AADLKSTQNAIDEITNKVNSVIEKMNTQFTAVGKEFNHLEKRIENLNKKVDDGFLDIWTYNAELLVLLENERTLDYH
DSNVKNLYEKVRSQLKNNAKEIGNGCFEFYHKCDNTCMESVKNGTYDYPKYSEEAKLNREEIDGVKLESTRIYQILA
IYSTVASSLVLVVSLGAISFWMCSNGSLQCRICI*
```

Figure 18, Schematic representation of construct number 484 (2X35S/CPMV HT)

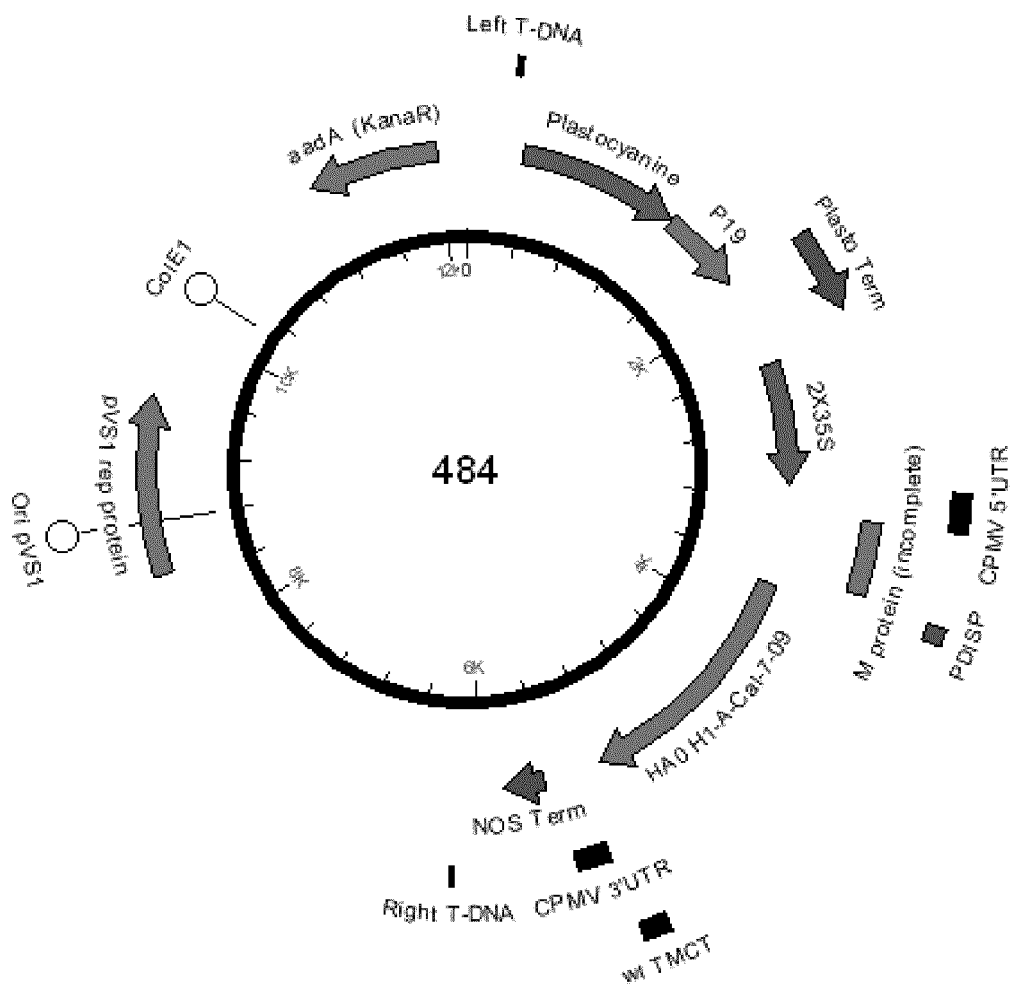

SEQUENCE LISTING

<160> NUMBER OF SEQ ID NOS: 6

<210> SEQ ID NO 1
<211> LENGTH: 48
<212> TYPE: DNA
<213> ORGANISM: Artificial Sequence
<220> FEATURE:
<223> OTHER INFORMATION: Primer IF-PDI.S1+3c

<400> SEQUENCE: 1
aaatttgtcg ggcccatggc gaaaaacgtt gcgattttcg gcttattg            48

<210> SEQ ID NO 2
<211> LENGTH: 46
<212> TYPE: DNA
<213> ORGANISM: Artificial Sequence
<220> FEATURE:
<223> OTHER INFORMATION: Primer IF-H1cTMCT.S1-4r

<400> SEQUENCE: 2
actaaagaaa ataggccttt aaatacatat tctacactgt agagac              46

<210> SEQ ID NO 3
<211> LENGTH: 1722
<212> TYPE: DNA
<213> ORGANISM: Artificial Sequence
<220> FEATURE:
<223> OTHER INFORMATION: PDISP/H1 California

<400> SEQUENCE: 3
atggcgaaaa acgttgcgat tttcggctta ttgtttctc ttcttgtgtt ggttccttct        60
cagatcttcg ctgacacatt atgtataggt tatcatgcga acaattcaac agacactgta      120
gacacagtac tagaaaagaa tgtaacagta acacactctg ttaaccttct agaagacaag      180
cataacggga actatgcaa actaagaggg gtagccccat tgcatttggg taatgtaac        240 attgctggct ggatcctggg aaatccagag tgtgaatcac tctccacagc aagctcatgg     300
tcctacattg tggaaacacc tagttcagac aatggaacgt gttacccagg agatttcatc    360
gattatgagg agctaagaga gcaattgagc tcagtgtcat catttgaaag gtttgagata   420
ttccccaaga caagttcatg gcccaatcat gactcgaaca aggtgtaac ggcagcatgt      480 cctcatgctg agcaaaaag cttctacaaa aatttaatat ggctagttaa aaaggaaat      540 tcatacccaa agctcagcaa atcctacatt aatgataaag ggaagaagt cctcgtgcta    600 tggggcattc accatccatc tactagtgct gaccaacaaa gtctctatca gaatgcagat    660
gcatatgttt ttgtggggtc atcaagatac agcaagaagt tcaagccgga atagcaata    720 agacccaaag tgagggatca agaagggaga atgaactatt actggacact agtagagccg   780
ggagacaaaa taacattcga agcaactgga atctagtgg taccgagata tgcattcgca    840
atggaaagaa atgctggatc tggtattatc atttcagata caccagtcca cgattgcaat   900
acaacttgtc aaacacccaa gggtgctata aacaccagcc tcccatttca gaatatacat   960
ccgatcacaa ttggaaaatg tccaaatat gtaaaagca caaaattgag actggccaca       1020
ggattgagga atatcccgtc tattcaatct agaggactat ttgggccat gccggttc      1080 attgaagggg ggtggacagg gatggtagat ggatggtacg gttatcacca tcaaaatgag    1140
caggggtcag gatatgcagc cgacctgaag agcacacaga atgccattga cgagattact    1200
aacaaagtaa attctgttat tgaaaagatg aatacacagt tcacagcagt aggtaaagag    1260
ttcaaccacc tggaaaaaag aatagagaat ttaaataaaa aagttgatga tggtttcctg   1320

```
gacatttgga cttacaatgc cgaactgttg gttctattgg aaaatgaaag aactttggac   1380
taccacgatt caaatgtgaa gaacttatat gaaaaggtaa aagccagct  aaaaaacaat   1440 gccaaggaaa ttggaaacgg ctgctttgaa ttttaccaca aatgcgataa cacgtgcatg   1500
gaaagtgtca aaaatgggac ttatgactac ccaaaatact cagaggaagc aaaattaaac   1560
agagaagaaa tagatggggt aaagctggaa tcaacaagga tttaccagat tttggcgatc   1620
tattcaactg tcgccagttc attggtactg gtagtctccc tgggggcaat cagtttctgg   1680
atgtgctcta atgggtctct acagtgtaga atatgtattt aa                     1722
```

<210> SEQ ID NO 4
<211> LENGTH: 4903
<212> TYPE: DNA
<213> ORGANISM: Artificial Sequence
<220> FEATURE:
<223> OTHER INFORMATION: Construct 1191 2X35S/CPMV-HT/NOS

<400> SEQUENCE: 4

```
tggcaggata tattgtggtg taaacaaatt gacgcttaga caacttaata acacattgcg     60 gacgtttta  atgtactgaa ttaacgccga atcccgggct ggtatattta tatgttgtca    120
aataactcaa aaccataaa  agtttaagtt agcaagtgtg tacatttta  cttgaacaaa    180 aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattatta    600 atgaattgat gaaagagttg gattaaagtt gtattagtaa ttagaatttg gtgtcaaatt    660
taatttgaca tttgatcttt tcctatatat tgccccatag agtcagttaa ctcatttta    720 tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctaggaac  aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaaggaga   1560
tgccctgaag gtactcaaac cttcgaaaaa gaaagcgagt aagttaaaat gcttcttcgt   1620
```

```
ctcctattta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaatatcaa agatacagtc tcagaagacc aaagggcaat    2220
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
cgataaagga aaggccatcg ttgaagatgc ctctgccgac agtggtccca aagatggacc    2400
cccacccacg aggagcatcg tggaaaaaga agacgttcca accacgtctt caaagcaagt    2460
ggattgatgt gataacatgg tggagcacga cacacttgtc tactccaaaa atatcaaga    2520 tacagtctca gaagaccaaa gggcaattga cttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaggaaag gccatcgttg aagatgcctc    2700
tgccgacagt ggtcccaaag atggaccccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct atataaggaa gttcatttca    2880
tttggagagg tattaaaatc ttaataggtt ttgataaaag cgaacgtggg gaaacccgaa    2940
ccaaaccttc ttctaaactc tctctcatct ctccttaaag caaacttctct cttgtctttc    3000 ttgcgtgagc gatcttcaac gttgtcagat cgtgcttcgg caccagtaca acgttttctt    3060
tcactgaagc gaaatcaaag atctctttgt ggacacgtag tgcggcgcca ttaaataacg    3120
tgtacttgtc ctattcttgt cggtgtggtc ttgggaaaag aaagcttgct ggaggctgct    3180
gttcagcccc atacattact tgttacgatt ctgctgactt tcggcgggtg caatatctct    3240
acttctgctt gacgaggtat tgttgcctgt acttcttttct tcttcttctt gctgattggt    3300
tctataagaa atctagtatt ttctttgaaa cagagttttc ccgtggtttt cgaacttgga    3360
gaaagattgt taagcttctg tatattctgc ccaaatttgt cgggcccgcg gatggcgaaa    3420
aacgttgcga ttttcggctt attgttttct cttcttgtgt tggttccttc tcagatcttc    3480
gcctgcaggc tcctcagcca aaacgacacc cccatctgtc tatccactgg cccctggatc    3540
tgctgcccaa actaactcca tggtgaccct gggatgcctg gtcaagggct atttccctga    3600
gccagtgaca gtgacctgga actctggatc cctgtccagc ggtgtgcaca ccttcccagc    3660
tgtcctgcag tctgacctct acactctgag cagctcagtg actgtcccct ccagcacctg    3720
gcccagcgag accgtcacct gcaacgttgc ccacccggcc agcagcacca aggtggacaa    3780
gaaaattgtg cccagggatt gtggttgtaa gccttgcata tgtacagtcc cagaagtatc    3840
atctgtcttc atcttccccc caaagcccaa ggatgtgctc accattactc tgactcctaa    3900
ggtcacgtgt gttgtggtag acatcagcaa ggatgatccc gaggtccagt tcagctggtt    3960
tgtagatgat gtggaggtgc acacagctca gacgcaaccc cgggaggagc agttcaacag    4020
```

| | | |
|---|---|---|
| cactttccgc tcagtcagtg aacttcccat catgcaccag gactggctca atggcaagga | 4080 |
| gcgatcgctc accatcacca tcaccatcac catcaccatt aaaggcctat tttctttagt | 4140 |
| ttgaatttac tgttattcgg tgtgcatttc tatgtttggt gagcggtttt ctgtgctcag | 4200 |
| agtgtgttta ttttatgtaa tttaatttct ttgtgagctc ctgtttagca ggtcgtccct | 4260 |
| tcagcaagga cacaaaaaga ttttaattttt attaaaaaaa aaaaaaaaaa agaccgggaa | 4320 |
| ttcgatatca agcttatcga cctgcagatc gttcaaacat ttggcaataa agtttcttaa | 4380 |
| gattgaatcc tgttgccggt cttgcgatga ttatcatata atttctgttg aattacgtta | 4440 |
| agcatgtaat aattaacatg taatgcatga cgttatttat gagatgggtt tttatgatta | 4500 |
| gagtcccgca attatacatt taatacgcga tagaaaacaa aatatagcgc gcaaactagg | 4560 |
| ataaattatc gcgcgcggtg tcatctatgt tactagatct ctagagtctc aagcttggcg | 4620 |
| cgcccacgtg actagtggca ctggccgtcg ttttacaacg tcgtgactgg gaaaaccctg | 4680 |
| gcgttaccca acttaatcgc cttgcagcac atccccettt cgccagctgg cgtaatagcg | 4740 |
| aagaggcccg caccgatcgc ccttcccaac agttgcgcag cctgaatggc gaatgctaga | 4800 |
| gcagcttgag cttggatcag attgtcgttt cccgccttca gtttaaacta tcagtgtttg | 4860 |
| acaggatata ttggcgggta aacctaagag aaaagagcgt tta | 4903 |

<210> SEQ ID NO 5
<211> LENGTH: 3462
<212> TYPE: DNA
<213> ORGANISM: Artificial Sequence
<220> FEATURE:
<223> OTHER INFORMATION: Cassette 484 from 2X35S promoter to NOS
      terminator

<400> SEQUENCE: 5

| | | |
|---|---|---|
| gtcaacatgg tggagcacga cacacttgtc tactccaaaa atatcaaaga tacagtctca | 60 |
| gaagaccaaa gggcaattga acttttcaa caaagggtaa tatccggaaa cctcctcgga | 120 |
| ttccattgcc cagctatctg tcactttatt gtgaagatag tggaaaagga aggtggctcc | 180 |
| tacaaatgcc atcattgcga taaggaaag gccatcgttg aagatgcctc tgccgacagt | 240 |
| ggtcccaaag atggaccccc acccacgagg agcatcgtgg aaaaagaaga cgttccaacc | 300 |
| acgtcttcaa agcaagtgga ttgatgtgat aacatggtgg agcacgacac acttgtctac | 360 |
| tccaaaaata tcaaagatac agtctcagaa gaccaagggg caattgagac ttttcaacaa | 420 |
| agggtaatat ccggaaacct cctcggattc cattgcccag ctatctgtca ctttattgtg | 480 |
| aagatagtgg aaaaggaagg tggctcctac aaatgccatc attgcgataa aggaaaggcc | 540 |
| atcgttgaag atgcctctgc cgacagtggt cccaaagatg gacccccacc cacgaggagc | 600 |
| atcgtggaaa agaagacgt tccaaccacg tcttcaaagc aagtggattg atgtgatatc | 660 |
| tccactgacg taagggatga cgcacaatcc cactatcctt cgcaagaccc ttcctctata | 720 |
| taaggaagtt catttcattt ggagaggtat taaaatctta ataggttttg ataaaagcga | 780 |
| acgtggggaa acccgaacca aaccttcttc taaactctct ctcatctctc ttaaagcaaa | 840 |
| cttctctctt gtcttcttg cgtgagcgat cttcaacgtt gtcagatcgt gcttcggcac | 900 |
| cagtacaacg ttttctttca ctgaagcgaa atcaaagatc tctttgtgga cacgtagtgc | 960 |
| ggcgccatta aataacgtgt acttgtccta ttcttgtcgg tgtggtcttg ggaaaagaaa | 1020 |
| gcttgctgga ggctgctgtt cagccccata cattacttgt tacgattctg ctgactttcg | 1080 |
| gcgggtgcaa tatctctact tctgcttgac gaggtattgt tgcctgtact tctttcttct | 1140 |

```
tcttcttgct gattggttct ataagaaatc tagtattttc tttgaaacag agttttcccg      1200
tggttttcga acttggagaa agattgttaa gcttctgtat attctgccca aatttgtcgg      1260
gcccatggcg aaaaacgttg cgattttcgg cttattgttt tctcttcttg tgttggttcc      1320
ttctcagatc ttcgctgaca cattatgtat aggttatcat gcaacaatt caacagacac       1380 tgtagacaca gtactagaaa agaatgtaac agtaacacac tctgttaacc ttctagaaga      1440
caagcataac gggaaactat gcaaactaag aggggtagcc ccattgcatt tgggtaaatg      1500
taacattgct ggctggatcc tgggaaatcc agagtgtgaa tcactctcca cagcaagctc      1560
atggtcctac attgtggaaa cacctagttc agacaatgga acgtgttacc caggagattt      1620
catcgattat gaggagctaa gagagcaatt gagctcagtg tcatcatttg aaaggtttga      1680
gatattcccc aagacaagtt catggcccaa tcatgactcg aacaaaggtg taacggcagc      1740
atgtcctcat gctggagcaa aaagcttcta caaaaattta atatggctag ttaaaaaagg      1800
aaattcatac ccaaagctca gcaaatccta cattaatgat aaagggaaag aagtcctcgt      1860
gctatggggc attcaccatc catctactag tgctgaccaa caaagtctct atcagaatgc      1920
agatgcatat gttttgtgg ggtcatcaag atacagcaag aagttcaagc cggaaatagc       1980
aataagaccc aaagtgaggg atcaagaagg gagaatgaac tattactgga cactagtaga      2040
gccgggagac aaaataacat cgaagcaac tggaaatcta gtggtaccga gatatgcatt       2100
cgcaatggaa agaaatgctg gatctggtat tatcatttca gatacaccag tccacgattg      2160
caatacaact tgtcaaacac ccaagggtgc tataaacacc agcctcccat ttcagaatat      2220
acatccgatc acaattggaa aatgtccaaa atatgtaaaa agcacaaaat tgagactggc      2280
cacaggattg aggaatatcc cgtctattca atctagagga ctatttgggg ccattgccgg      2340
tttcattgaa ggggggtgga cagggatggt agatggatgg tacggttatc accatcaaaa      2400
tgagcagggg tcaggatatg cagccgacct gaagagcaca cagaatgcca ttgacgagat      2460
tactaacaaa gtaaattctg ttattgaaaa gatgaataca cagttcacag cagtaggtaa      2520
agagttcaac cacctggaaa aagaataga gaatttaaat aaaaaagttg atgatggttt       2580
cctggacatt tggacttaca atgccgaact gttggttcta ttggaaaatg aaagaacttt      2640
ggactaccac gattcaaatg tgaagaactt atatgaaaag gtaagaagcc agctaaaaaa      2700
caatgccaag gaaattggaa acggctgctt tgaattttac cacaaatgcg ataacacgtg      2760
catggaaagt gtcaaaaatg ggacttatga ctacccaaaa tactcagagg aagcaaaatt      2820
aaacagagaa gaaatagatg gggtaaagct ggaatcaaca aggatttacc agattttggc      2880
gatctattca actgtcgcca gttcattggt actggtagtc tccctggggg caatcagttt      2940
ctggatgtgc tctaatgggt ctctacagtg tagaatatgt atttaaaggc ctatttctt      3000 tagtttgaat ttactgttat tcggtgtgca tttctatgtt tggtgagcgg ttttctgtgc      3060
tcagagtgtg tttattttat gtaatttaat ttctttgtga gctcctgttt agcaggtcgt      3120
cccttcagca aggacacaaa aagattttaa ttttattaaa aaaaaaaaaa aaaagaccg       3180 ggaattcgat atcaagctta tcgacctgca gatcgttcaa acatttggca ataaagttc      3240 ttaagattga atcctgttgc cggtcttgcg atgattatca tataatttct gttgaattac      3300
gttaagcatg taataattaa catgtaatgc atgacgttat ttatgagatg gttttatg       3360 attagagtcc cgcaattata catttaatac gcgatagaaa acaaaatata gcgcgcaaac      3420
taggataaat tatcgcgcgc ggtgtcatct atgttactag at                        3462
```

```
<210> SEQ ID NO 6
<211> LENGTH: 573
<212> TYPE: PRT
<213> ORGANISM: Artificial Sequence
<220> FEATURE:
<223> OTHER INFORMATION: Amino acid sequence of PDISP/H1 California

<400> SEQUENCE: 6

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365
```

-continued

```
Val Asp Gly Trp Tyr Gly Tyr His His Gln Asn Glu Gln Gly Ser Gly
    370             375             380
Tyr Ala Ala Asp Leu Lys Ser Thr Gln Asn Ala Ile Asp Glu Ile Thr
385             390             395             400
Asn Lys Val Asn Ser Val Ile Glu Lys Met Asn Thr Gln Phe Thr Ala
            405             410             415
Val Gly Lys Glu Phe Asn His Leu Glu Lys Arg Ile Glu Asn Leu Asn
            420             425             430
Lys Lys Val Asp Asp Gly Phe Leu Asp Ile Trp Thr Tyr Asn Ala Glu
        435             440             445
Leu Leu Val Leu Leu Glu Asn Glu Arg Thr Leu Asp Tyr His Asp Ser
450             455             460
Asn Val Lys Asn Leu Tyr Glu Lys Val Arg Ser Gln Leu Lys Asn Asn
465             470             475             480
Ala Lys Glu Ile Gly Asn Gly Cys Phe Glu Phe Tyr His Lys Cys Asp
            485             490             495
Asn Thr Cys Met Glu Ser Val Lys Asn Gly Thr Tyr Asp Tyr Pro Lys
        500             505             510
Tyr Ser Glu Glu Ala Lys Leu Asn Arg Glu Glu Ile Asp Gly Val Lys
        515             520             525
Leu Glu Ser Thr Arg Ile Tyr Gln Ile Leu Ala Ile Tyr Ser Thr Val
        530             535             540
Ala Ser Ser Leu Val Leu Val Val Ser Leu Gly Ala Ile Ser Phe Trp
545             550             555             560
Met Cys Ser Asn Gly Ser Leu Gln Cys Arg Ile Cys Ile
            565             570
```

US 11,959,088 B2

MODIFYING PROTEIN PRODUCTION IN PLANTS

FIELD OF INVENTION

The present invention relates to methods of producing protein in plants. The present invention also provides methods to increase the production of one or more proteins in plants.

BACKGROUND OF THE INVENTION

Plant-based protein expression platforms are a useful answer to the growing demand for biological therapeutics and diagnostics worldwide. Plant cells, unlike bacteria or yeast, can correctly fold, assemble and modify complex proteins of mammalian origin, such as therapeutic and diagnostic antibodies. Plants also present advantages in terms of safety, capital investment, and ease of scaling-up compared to mammalian cell-based production systems.

Therefore, plants are suitable hosts for the production of proteins which have current applications in life sciences such as for example mAbs or viral antigens such as HA from influenza.

WO 07016276 discloses a method for the stable transformation of plants by cutting a seedling at the point where the two cotyledons meet to remove both cotyledons and initial true leaves and to allow emergence of a new shoot from the cut surface. This method involves wounding the plant to facilitate the introduction of *Agrobacterium* at the wound site and increase the efficiency of transformation. The cut seedlings are vortexed in a suspension of bacterium, which comprises a transformation plasmid that carries a desired transfer DNA. The step of wounding is required prior to the step of transformation. Precise cutting-mediated transformation can result in the stable transformation of new shoots that arise from the cut surface of seedlings. These shoots can develop into the above-ground portions of a plant and consequently give rise to transformed progenies.

Spokevicus et al (Functional Plant Biology 2006) disclose the in vivo transformation of dormant lateral buds (DLBs) in *Populus* trees. DLBs were either wounded by a central vertical cut or the top of plants were removed and the remaining DLBs were treated by a combination of vertical cut, addition of protective covering or addition of *A. tumefaciens*. With this method, the step of wounding is required prior to the step of transformation.

WO 2008/151444 discloses a method of synthesizing a protein of interest within a plant using a transient expression system. The plant were pruned before infiltration of the desired nucleic acid construct. Apical and axillary buds of *N. benthamiana* plants were either mechanically removed from plants by pinching, or chemically pruned prior to vacuum infiltrating of the leaves, with *Agrobacterium* strains transformed with appropriate plasmids.

Wydro et al. 2006 (Acta Biochimica *Polonica*, Vol 53 No. 2/2006 289-298) discloses that the highest level of transient green fluorescent protein (GFP) gene expression is detected in the youngest leaves (located at the top of the plant) of *N. benthamiana* infiltrated with *A. tumefaciens*, whereas the expression in older leaves, positioned at intermediate and bottom position is lower. Halfhill et al. (Plant Cell Rep 22: 338-343, 2003) suggested that changes in GFP fluorescence were related to changes in the concentration of soluble proteins during leaf ageing. The level of gfp gene expression and concentration of soluble proteins declined at similar times and to similar extents in individual leaves at different positions. Wydro et al. suggests that the close relationship between these two factors would suggest that the decline in GFP expression was a result of general changes in leaf physiology.

The expression of clinically useful proteins in plants has been bolstered by the development of high-yielding systems for transient protein expression using agroinfiltration. There is a need to optimize expression and increase the quantity and quality of recombinant proteins in plants.

SUMMARY OF THE INVENTION

The present invention relates to methods of producing protein in plants. The present invention also provides methods to increase the production of one or more proteins in plants.

It is an object of the invention to provide an improved method for producing protein in plants.

The present invention provides a method for producing a protein of interest within a plant or portion of a plant comprising:
 a) treating the plant or portion of the plant to increase secondary leaf biomass production in the plant or portion of the plant;
 b) introducing one or more than one nucleic acid into the plant or portion of the plant, the nucleic acid comprising a nucleotide sequence encoding the protein of interest, the nucleotide sequence operatively linked to a regulatory region that is active in the plant;
 c) incubating the plant or portion of the plant under conditions that permit the expression of the nucleotide sequence encoding the protein of interest thereby producing the protein of interest, wherein, the yield of the protein of interest is increased when compared with the yield of the protein of interest obtained from the same plant tissue of a similar plant that is grown under the same conditions, but that has not been treated to increase the secondary leaf biomass.

The protein of interest that may be used in the method as described above, may be an antibody, an antigen, a vaccine or an enzyme. The protein of interests may be an influenza HA protein and the HA may form influenza virus-like particle (VLP) when expressed in the plant or portion of the plant.

The one or more than one nucleic acid may be introduced in the plant or portion of the plant that has a ratio of secondary biomass to primary leaf biomass of between 0.2:1 and 3:1.

The present invention also provides the method as described above, wherein in the step of treating, step a), is carried out from about 40 days prior to the step of introducing the one or more than one nucleic acid up to the day of introducing the one or more than one nucleic acid, or from about 40 days prior to the step of introducing one or more than one nucleic acid up to the day of harvesting the plant or portion of the plant. The present invention includes the method described above wherein the step of treating the plant, step a), comprises increasing light duration during growth of the plant, increasing light intensity during growth of the plant, select wavelengths that a plant is exposed to during growth, pruning of the apical bud of the primary stem of the plant, cultivating the plant in the presence of an agent, a hormone, or a combination thereof, that increases secondary shoot development, applying a chemical compound that reduces apical dominance, mechanical pruning, chemical pruning, genetic modification knock-in, knock-out, and plant breeding to encourage secondary growth, or a combination thereof.

In the method described above the plant may be cultivated in the presence of a phytohormone. For example the plant may be cultivated in the presence of about 50 ppm to 900 ppm of phytothormon. The phytohormon may be a synthetic cytokinin for example 6-benzylaminopurine (BAP).

The present invention also includes the method described above wherein the method further comprises a step of harvesting the plant and optionally, purifying the protein of interest. During the step of harvesting, the secondary leaves, or the primary leaves and secondary leaves, may be harvested. Furthermore, secondary leaves, intermediate leaves from primary stems (P2), and young leaves from primary stems (P1), may be harvested, or intermediate leaves from primary stems (P2), young leaves from primary stems (P1), old leaves from secondary stems (S3), intermediate leaves from secondary stems (S2) and young leaves from secondary stems (S1) may be harvested. Furthermore, old leaves (P3) from primary stems of the plant may be excluded from harvesting.

The present invention provides the method as described above wherein in the step of introducing, step b), the nucleic acid is transiently expressed in the plant or the nucleic acid is stably expressed in the plant.

By increasing the secondary leaf biomass an increase in protein yield from primary and secondary biomass may be obtained when compared with the yield of the protein of interest obtained from the same plant tissue of a plant that has not been treated to increase the secondary biomass and grown under the same conditions.

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 12A and 12B show primers IF-PDI.S1+3c (SEQ ID NO: 1) and IF-H1cTMCT.S1-4r (SEQ ID NO: 2), respectively.

FIG. 13 shows the nucleotide sequence of PDISP/H1 California (SEQ ID NO:3).

FIG. 14 shows a schematic representation of construct 1191

FIG. 15 shows the nucleotide sequence for construct 1191 (SEQ ID NO:4). The tDNA boarders are underlined.

FIG. 16 shows the nucleotide sequence for expression cassette 484. The sequence encoding PDISP/H1 California is underlined.

FIG. 17 shows the amino acid sequence of PDISP/H1 California (SEQ ID NO:6)

FIG. 18 shows a schematic representation of construct number 484 (2X35S/CPMV HT)

DETAILED DESCRIPTION

Figure 1:
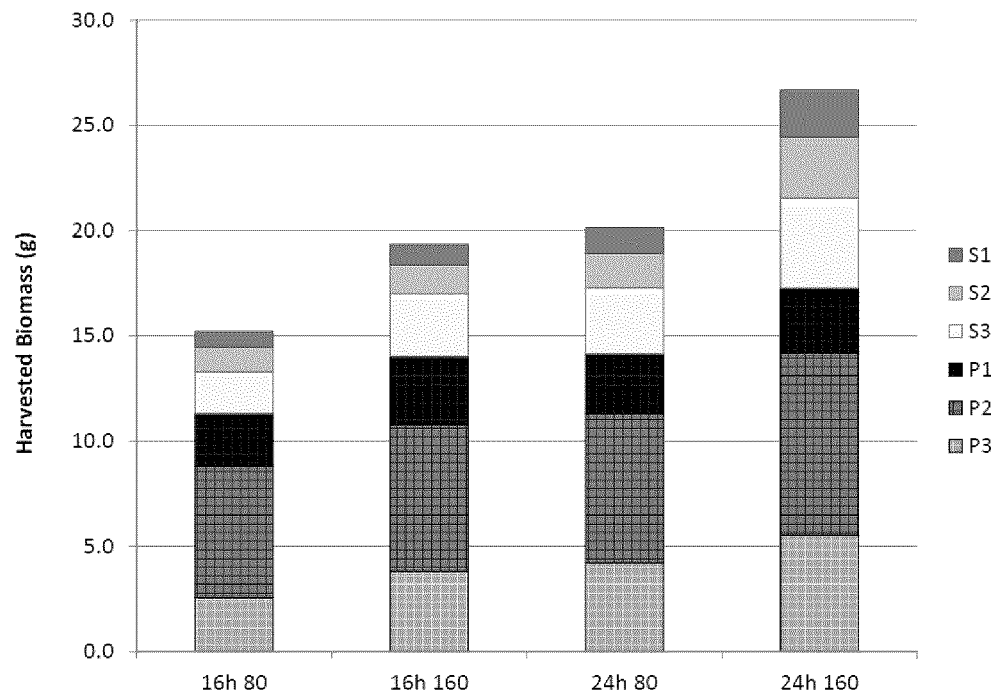
FIG. 1 shows the biomass production of plants grown in a green house before infiltration under different light photoperiods (16 h and 24 h) and light intensity treatments (80 and 160 µmol/m2·s). Young (P1), mature (P2) and old (P3) leaves of the main stem and young (S1), mature (S2) and old (S3) leaves of secondary stems were harvested and the biomass was determined.

The present invention relates to methods of producing protein in plants. The present invention also provides methods and compositions for the production of proteins of interest in plants. A method for producing a protein of interest within a plant or a portion of a plant is also provided.

The present invention provides a method for producing a protein of interest within a plant or portion of a plant comprising:
   a) treating the plant or portion of the plant to increase secondary leaf biomass production in the plant or portion of the plant;
   b) introducing one or more than one nucleic acid into the plant or portion of the plant, the nucleic acid comprising a nucleotide sequence encoding the protein of interest, the nucleotide sequence operatively linked to a regulatory region that is active in the plant;
   c) incubating the plant or portion of the plant under conditions that permit the expression of the nucleotide sequence encoding the protein of interest, thereby producing the protein of interest, wherein, the yield of the protein of interest is increased when compared with the yield of the protein of interest obtained from the same plant tissue of a similar plant that is grown under the same conditions, but that has not been treated to increase the secondary biomass.

The plant tissue may be harvested, and the protein of interest be extracted from the plant. If desired, the protein of interest may be purified using standard techniques that are well known in the art. Alternatively, the plant may be harvested and used as a food, nutrient or medical supplement or the plant may be partially processed to produce a minimally processed plant extract for use as a food, nutrient, or medical supplement.

By a "similar plant", it is meant a plant that is of the same genus, species and variety as the plant that is treated to increase secondary biomass production.

The one or more than one nucleic acid may be introduced in the plant or portion of plant when the ratio of the secondary leaf biomass to the primary leaf biomass is between 0.2:1 and 3:1 or any ration therebetween. For example, the ratio of the secondary leaf biomass to the primary leaf biomass may be from about 0.2:1, 0.3:1, 0.4:1, 0.5:1, 0.6:1, 0.7:1, 0.8:1, 0.9:1, 1:1, 1.2:1, 1.4:1, 1.6:1, 1.8:1, 2:1, 2.2:1, 2.4:1, 2.6:1, 2.8:1, 3:1 or any ratio therebetween.

The protein of interest may be any protein for example, an enzyme, a pharmaceutically active protein, a blood coagulation factor, an antibody, an antigen, a vaccine, a food supplement, a nutritional supplement, an industrial enzyme, or one or more proteins that may form "virus like particle" within the plant.

The term "virus like particle" (VLP), or "virus-like particles" or "VLPs" refers to structures that self-assemble and comprise structural proteins such as influenza HA protein. VLPs are generally morphologically and antigenically similar to virions produced in an infection, but lack genetic information sufficient to replicate and thus are non-infectious. In some examples, VLPs may comprise a single protein species, or more than one protein species. See for example WO2009/009876; WO2009/076778; WO 2010/003225 (each of which is herein incorporated by reference).

The present invention therefore further relates to methods of producing VLPs in plants. The present invention also provides methods and compositions for the production of VLPs in plants. For example, a method for producing virus like particles (VLPs) within a plant or portion of a plant is provided that comprises:
  a) treating the plant or portion of the plant to increase secondary leaf biomass production in the plant or portion of the plant;
  b) introducing one or more than one nucleic acid into the plant or portion of the plant, the nucleic acid comprising a nucleotide sequence encoding a hemagglutinin (HA), the nucleotide sequence operatively linked to a regulatory region that is active in the plant;
  c) incubating the plant or portion of the plant under conditions that permit the expression of the nucleotide sequence encoding the HA, thereby producing the HA, wherein, the yield of the HA is increased when compared with the yield of the HA obtained from the same plant tissue of a similar plant that is grown under the same conditions, and that has not been treated to increase the secondary biomass.

The plant tissue may be harvested, and the VLPs extracted from the plant. If desired, the VLPs may be purified using standard techniques that are well known in the art (see for example WO2009/009876; WO2009/076778; WO 2010/003225; each of which is herein incorporated by reference). Alternatively, the plant may be harvested and used as a food, nutrient or medical supplement or the plant may be partially processed to produce a minimally processed plant extract for use as a food, nutrient, or medical supplement.

The one or more than one nucleic acid may be introduced in the plant or portion of plant when the ratio of the secondary leaf biomass to the primary leaf biomass is between 0.2:1 and 3:1 or any ration therebetween. For example, the ratio of the secondary leaf biomass to the primary leaf biomass may be from about 0.2:1, 0.3:1, 0.4:1, 0.5:1, 0.6:1, 0.7:1, 0.8:1, 0.9:1, 1:1, 1.2:1, 1.4:1, 1.6:1, 1.8:1, 2:1, 2.2:1, 2.4:1, 2.6:1, 2.8:1, 3:1 or any ratio therebetween.

As shown in FIG. 7 a plant 10, comprises a primary stem 20, an apical bud 40, and leaves (P1, P2, P3, and S1, S2 and S3) that emerge from the primary stem 20. New leaves that emerge near the apex 40 of plant 10 are termed P1. P1 leaves, or upper leaves are still growing and increasing their biomass. P1 leaves are positioned above P2 leaves along the main stem, and include very young leaves of the 'apex complex' (i.e. the apical bud and any newly forming leaves), when this complex is present. The P1 leaves of young plants, for example 25 to 30-day old plants, usually correspond to Leaf 1, Leaf 2 and the apex complex. P2 leaves refers to mature leaves that have not yet started to senesce. P2 leaves include leaves that are near completion of, or have completed, their expansion phase. Looking at a plant from above, P2 leaves are the biggest leaves that are visible, and may mask or cover P3 leaves. P2 leaves typically correspond to leaf 3, leaf 4 and leaf 5 on the main stem, (leaf numbering starts at the top, or apex of the plant; see FIG. 2A of Robert et al. 2013, PLoS ONE 8(7):e70203, doi:10.1371/journal.pone.0070203; which is herein incorporated by reference). P3 leaves, or bottom leaves, are leaves that are positioned below P2 leaves on the main stem. P3 leaves include, but are not restricted to, senescing leaves that may exhibit some yellowing. P3 leaves often include Leaf 5, Leaf 6, Leaf 7, and older leaves of the plant. Symptoms of senescence (e.g. loss of chlorophyll) are often visible from Leaf 7 or Leaf 8. Leaves 5 and 6 do not look senescent but often contain low amounts of protein.

S1, S2 and S3 leaves are attached to secondary (and eventually tertiary) stems. S1 leaves are those leaves that are attached to secondary stems that emerge from P1 leaves. These secondary leaves are close to the apex, and younger than S2 and S3 leaves. S2 leaves are attached to secondary stems emerged from P2 leaves, and S3 leaves are attached to secondary stems emerged from P3 leaves. S3 leaves are the oldest secondary leaves, but as they are younger they are more efficient than P3 leaves in producing proteins.

It has been found that by increasing the secondary leaf biomass in a plant the overall yield of a protein of interest increases. Using the methods described herein, high yields of the protein of interest have been produced when the production of protein of interest is compared to producing the same protein of interest in a plant using a similar transformation protocol, and exposed to similar growth conditions, but that does not treat the plant or portion of the plant to increase the secondary leaf biomass, prior to the step of introducing the nucleic acid into the plant.

As shown in FIG. 8, removal of the apex of a plant (pruning of the plant), leads to an increase in yield of the protein of interest (hemagglutinin; HA) per plant in secondary stems (S) and a decrease in yield of the protein of interest (HA) per plant in primary stems (P), when compared to plants where the apex had not been removed. Furthermore, removal of the apex of the plant resulted in a 2.1 fold increase in secondary leaf biomass, a decrease in the primary leaf biomass, with a secondary leaf biomass to primary leaf biomass increasing from 0.4:1 to 1.6:1 (see Table 3; Example 5).

By an increase of yield of protein of interest, it is meant an increase in yield of the protein of interest by about 5% to about 500% (i.e. up to a 5 fold increase), or any amount therebetween as determined using standard techniques in the art, for example, from about 10% to about 50% or any value therebetween for example about 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, 100, 110, 120, 130, 140, 150, 160, 170, 180, 200, 220, 240, 260, 280, 300, 320, 340, 360, 380, 400, 420, 440, 460, 480 or 500%, when compared to the yield of a protein of interest expressed in a plant wherein the plant was not treated to increase the secondary leaf biomass.

By an increase in secondary leaf biomass, it is meant an increase in secondary leaf biomass by about 2% to about 300%, or any amount therebetween (i.e. up to a 3 fold increase) as determined using standard techniques in the art, for example, from about 10% to about 200% or any value therebetween for example about 2, 5, 8, 10, 12, 15, 18, 20, 22, 24, 25, 26, 28, 30, 32, 34, 35, 36, 38, 40, 42, 44, 45, 46, 48, 50, 52, 54, 55, 56, 58, 60, 65, 70, 75, 80, 85, 90, 95, 100, 110, 120, 130, 140, 150, 160, 170, 180, 200, 220, 240, 260, 280 or 300%, when compared to a similar plant (i.e. same plant variety) grown under the same conditions that was not treated to increase the secondary leaf biomass. Biomass may be determined using any technique as would be known to one of skill in the art, and may include determining fresh weight, dry weight, protein content, volume displacement and the like. Unless otherwise stated, "leaf biomass" means the biomass of the leaf and petiole. The increase in secondary leaf biomass may be a result of an increase in the number of secondary stems and leaves, an increase in the length of secondary stems and leaves, an increase in the volume of the leaf, an increase in the area of the leaf or a combination thereof.

Following the step of treating the plant, as set out in step a of the method provided above, the secondary leaf biomass may be between 20% to 50% of total biomass of the plant, or any amount therebetween. For example the percent ratio of secondary leaf biomass (relative to the tool biomass of the plant) may be 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48% or 49% or any amount therebetween.

As may be seen from FIGS. 2 to 6 and 8, the level of protein accumulation in the plant or portion of the plant is influenced by the ratio of secondary leaf biomass to primary leaf biomass for example from about 0.2:1 to about 1:1 (secondary leaf biomass:primary leaf biomass), or any amount therebetween, for example from about 0.2:1, 0.3:1, 0.4:1, 0.5:1, 0.6:1, 0.7:1, 0.8:1, 0.9:1, 1:1, 1.2:1, 1.4:1, 1.6:1, 1.8:1, 2:1, 2.2:1, 2.4:1, 2.6:1, 2.8:1, 3:1 or any ratio therebetween (secondary leaf biomass:primary leaf biomass), or any amount therebetween.

The ratio of secondary leaf biomass to primary leaf biomass in a plant may be varied by increasing the secondary leaf biomass compared to primary leaf biomass, by for example increasing light duration during growth of the plant, increasing light intensity during growth of the plant, pruning of the apical bud 40 (FIG. 7) of the plant, cultivating the plant in the presence of an agent that increases secondary biomass formation, a hormone that increases secondary biomass formation, applying a chemical compound that reduces apical dominance or a combination thereof.

Therefore the present invention also provides a method for increasing the yield of a protein of interest by modulating the ratio of secondary leaf biomass to primary leaf biomass by treating the plant to increase the secondary leaf biomass compared to a similar plant that has not been treated.

By primary leaf biomass (or primary biomass), it is meant the biomass of a plant that encompasses the biomass of primary leaves (P1, P2, P3 and associated petioles). Therefore primary leaf biomass does not comprise biomass from secondary leaves, or tertiary leaves, nor does it comprise biomass from roots.

Generally a stem (may also be termed shoot) provides an axis for buds, fruits, and leaves. One of the main structural axis of a vascular plant is the main or primary stem (20, FIG. 7). The primary stem 20 typically provides support for primary leaves (P1, P2, P3), flowers, buds, fruits and secondary stems 30. The primary leaf biomass comprises the biomass from primary leaves (P1, P2, P3) and their associated petioles.

By "secondary stem formation" it is meant either the initiation of new secondary stems, the development of already initiated secondary stems, or both the initiation and development of initiated secondary stems, that result in an increased proportion of secondary leaf biomass.

The primary stem of a plant may have leaves of different age directly extending from the primary stem 20. The leaves of the primary stem may be classified as old (P3), intermediate (P2) or young (P1), depending on the age of the leaf.

By secondary leaf biomass (or secondary biomass), it is meant the biomass of leaves and petioles obtained from secondary stems 30. More specifically secondary leaf biomass is biomass that does not comprise biomass from primary leaves, flowers, the apical bud 40, or roots. Secondary leaf biomass may also comprise leaf biomass derived from tertiary or other stems that emerge from the secondary stem 30.

"Secondary", "auxiliary", "axillary" or "lateral" stems may also extend from the main or primary stem 20 of a plant. Therefore a secondary stem 30 may comprise one or more secondary stems and one or more secondary leaves (S1, S2, S3). Furthermore a secondary stem may comprise one or more tertiary or other stems. The secondary stem 30 of a plant may have leaves of different age, and these leaves may be classified as young leaves (S1), intermediate leaves (S2) or old leaves (S3).

Treating the plant to increasing the secondary leaf biomass prior infiltration of the nucleic acid comprising a nucleotide sequence encoding the protein of interest has been found to increase the level of protein of interest expression (as a % of total synthesized protein) and yield (mg of protein/kg of fresh weight). Treatment of the plant to increase the secondary leaf biomass may include, but is not limited to, an increase in light intensity a plant is exposed to during growth and resulting in an increase in secondary growth, an increase in time a plant is exposed to light (light duration) during growth that results in an increase in secondary growth, select wavelengths that a plant is exposed to during growth so that there is an increase in secondary growth, varying the day/night temperature regime that results in an increase of secondary growth, for example varying the temperature from about +/−1 deg C. to about +/−15 deg C., or any amount therebetween from a base of 20 deg C., varying the temperature from about +/−1 deg C. to about +/−15 deg C., or any amount therebetween from a base of 20 deg C. for a period of time from about 5 min to about 16 hours, or any time therebetween, if a pulse of a different temperature is provided that is shorter than the dark or light period, then this pulse may be provided at the beginning or end of the photoperiod, for example providing a pulse of a different temperature from about 30 min to about 2 hours at the beginning or end of the photoperiod, or at the end of the photoperiod.

Furthermore, treatment of the plant to increase the secondary leaf biomass may include, but not limited to, culture in the presence of an agent to induce secondary stem, secondary biomass formation, or both, a hormone to induce secondary stem formation, secondary biomass formation, or both, applying a chemical compound that reduces apical dominance, pruning of the primary apical bud 40 to induce secondary stem formation, secondary biomass formation, or both, genetic modification for example, knock-in or knock-out of genes that result in an enhancement of secondary stem formation, secondary biomass formation, or both, plant breeding in combination with selection of plants exhibiting an increase in secondary growth when compared to their parental strains, or a combination thereof.

By "light" it is meant light comprising the spectrum of wavelengths that are utilized by the leaves of a plant, for example wavelengths from about 400 to about 700 nm or any wavelength therebetween, and may include the blue, green and red and if required, infra-red wavelength portions of the electromagnetic spectrum. Any suitable light source that emits wavelengths that may be utilized by the plant include for example, natural light, a ceramic metal halide source, a metal halide source, a high pressure sodium source, LEDs, a fluorescent source, an incandescent source, or a combination thereof.

The step of treating the plant to increase secondary leaf biomass before infiltration may be carried out throughout the plant growth cycle from germination (i.e. day 0) through to infiltration (i.e. introducing the recombinant vector into the plant), or the day of harvesting the plant, or any time therebetween. For example, if the treatment is a photoperiod of 24 hrs, then the germinated seedling may be exposed to this photoperiod for a treatment period that extends from the day of germination, though the step of plant transformation or infiltration, incubation of the transformed plant, and up to the day of harvest. However, shorter periods of treatment may also be used.

In a similar manner, the step of treating a plant to increase secondary growth may include an increase in light intensity that a plant is exposed to light during growth and that results in an increase in secondary growth. This treatment may be applied throughout the time of plant growth from germination, through plant transformation or infiltration, to the ay of harvesting the plant, or any time therebetween. Similarly, exposing plants to select wavelengths during growth so that result in an increase in secondary growth, may be applied throughout the time of plant growth from germination (i.e. day 0) through to infiltration (i.e introducing the recombinant vector into the plant), or the day of harvesting the plant, or any time therebetween. The day/night temperature regime may be varied (from about +/−1 deg C. to about +/−15 deg C., or any amount therebetween from a base of 20 deg C.; or pulses of carried temperature may be provided) to increase secondary plant growth, and the plant may be exposed to this treatment throughout the plant growth cycle from germination (i.e. day 0) through to infiltration (i.e introducing the recombinant vector into the plant), or the day of harvesting the plant, or any time therebetween.

Alternatively, other treatment methods to increase plant secondary leaf biomass may be applied before the step of transformation or infiltration may be from about 20 days prior to infiltration up to the day of infiltration, or any time in between, for example 20 days prior to infiltration, to the day of infiltration, or any time in between, for example from 20 days, 19 days, 18, days, 17 days, 16 days, 15 days, 14 days, 13 days, 12 days, 11 days, 10 days, 9 days, 8 days, 7 days, 6 days, 5 days, 4 days, 3 days, 2 days, 1 day prior to infiltration, to the day of infiltration, or any time in between.

The use of increasing light duration, to increase the secondary leaf biomass, involves exposing the plant from about 12 h to about 24 h of light or any value therebetween, for example about 12, 13, 14, 15, 16, 17, 18, 19, 20, 21, 22, 23 or 24 h. For example, the light duration may be of 24 h, so that the plant is exposed to constant light prior to the step of infiltration.

The increase in light duration may be carried out from about from the day of germination through to the day of infiltration, or to the day of harvesting the plant, or any time in between. For example which is not to be considered limiting from 40 days, 35 days, 30 days, 25 days, 20 days, 19 days, 18, days, 17 days, 16 days, 15 days, 14 days, 13 days, 12 days, 11 days, 10 days, 9 days, 8 days, 7 days, 6 days, 5 days, 4 days, 3 days, 2 days prior infiltration, the day or infiltration, the day of harvesting, or any time in between. One of skill can readily determine the appropriate interval prior to pruning.

Light intensity may include natural sun light, or natural sunlight supplemented with artificial light, or artificial light. If artificial light is used alone, or is used to supplement natural sunlight, then from about 60 ($\mu$mol/m2·s) to about 200 ($\mu$mol/m2·s) or any value therebetween for example about 60, 70, 80, 90, 100, 110, 120, 130, 140, 150, 160, 170, 180, 190 or 200 ($\mu$mol/m2·s), or any amount therebetween may be used. For example, the light intensity may be 160 ($\mu$mol/m2·s). The increase in light intensity may be carried out throughout the plant growth cycle from germination (i.e. day 0) through to infiltration (i.e introducing the recombinant vector into the plant), or the day of harvesting the plant, or any time therebetween. For example, from about, for example from about 40 days, 35 days, 30 days, 25 days, 20 days, 19 days, 18, days, 17 days, 16 days, 15 days, 14 days, 13 days, 12 days, 11 days, 10 days, 9 days, 8 days, 7 days, 6 days, 5 days, 4 days 3 days, 2 days, 1 day prior infiltration, the day of infiltration, the day of harvesting the plant, or any time in between. One of skill can readily determine the appropriate interval prior to pruning.

By pruning it is meant the removal of one or more than one apical bud 40, or removing the tip or upper portion of the stem that includes the apical bud 40. Pruning may also include killing, inducing necrosis, or reducing growth of the apical buds without removing the buds from the plant. By reduction of growth of the bud (or reducing bud growth), it is meant that the bud exhibits a reduction for example in the metabolic activity, or size increase over a defined period of time, of from about 50% to 100%, or any amount therebetween, when compared to a bud that has not been treated. Pruning may also be accomplished by applying a chemical compound that reduces apical dominance. If a chemical compound is applied for the purposes of pruning, then the dosages used are typically those as recommended by the manufacturer of the chemical compound.

Pruning can be accomplished by any means that would be known to one of skill in the art and includes, but is not limited to, mechanical removal of the bud, for example but not limited to, cutting, clipping, pinching, compression for example using tongs and the like, localized freezing for example by directing a localized stream of liquid nitrogen to the bud, or surrounding the bud with tongs or other device that has been cooled using an appropriate cold source including liquid nitrogen, dry ice, ethanol-dry ice, ice, and the like, so that the temperature of the bud is reduced so as to reduce growth of the bud, or kill the bud.

Pruning also includes chemical pruning, for example, applying a herbicide (chemical compound; pruning agent) that kills or reduces the growth of the bud, or applying a grow regulator that kills or reduces the growth of the bud. The use of chemical pruning permits an efficient manner of treatment of pruning as plants can be readily treated by spraying, misting, soaking, the chemical compound on the plant, or dipping the plants into a solution comprising the chemical compound. Plants may be treated once prior to the step of infiltration, or treated more than once prior to the step of infiltration. The agent, chemical compound, or hormone increases secondary stem formation, secondary biomass formation, or both, or reduces apical dominance or a combination thereof. For example the plant may be cultured or treated with cytokines or phytohormones that promote secondary stem formation or reduce apical dominance or a combination thereof. For example the plant may be treated with a phytohormone such for example with a cytokinins (CK) to increase to promote secondary stem formation. The cytokinin may for example be a synthetic cytokinin such as 6-Benzylaminopurine (BAP) also known as benzyl adenine.

A plant may be treated with a quantity of phytohormon from about 50 ppm to about 900 ppm or any amount there between, for example 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm or any amount therebetween. For example the plant may be treated with about 100 ppm to 500 ppm of a phytohormon for example BAP.

Figure 9A:
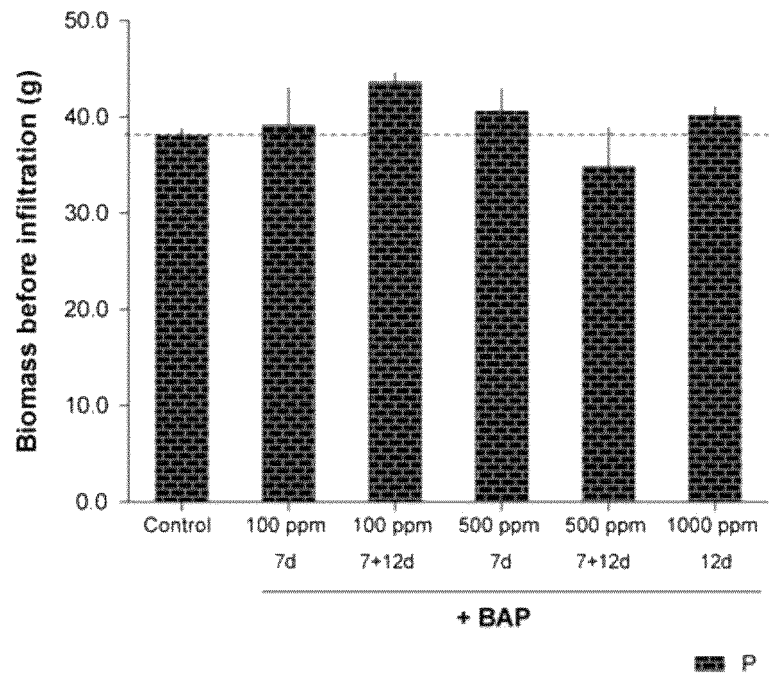
FIG. 9 shows the effect 6-benzylaminopurine (BAP) on total primary biomass (P) versus total secondary biomass (S), for plants treated with benzylaminopurine (BAP) at 100, 500 or 1,000 ppm concentration, 7 and/or 12 days after seedling transplantation.
Figure 9B:
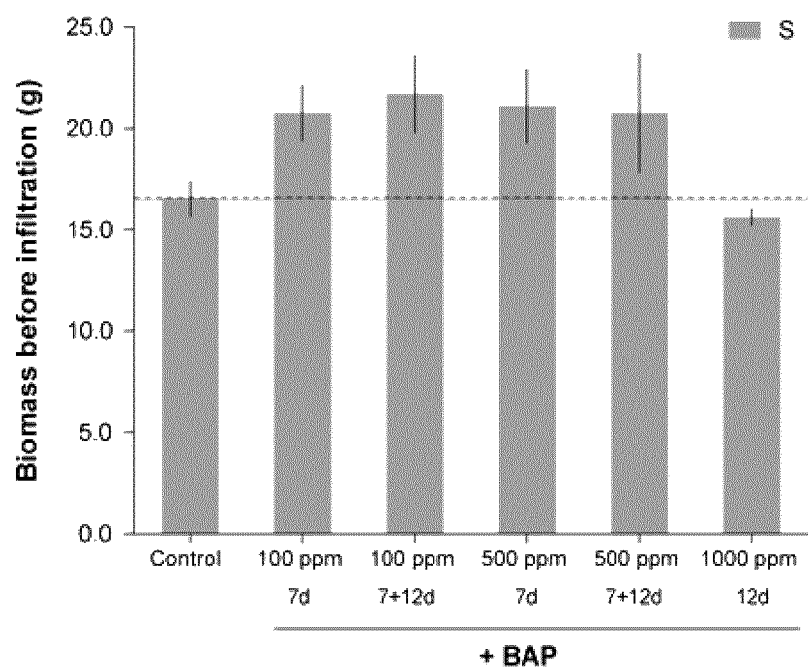
Figure 10:
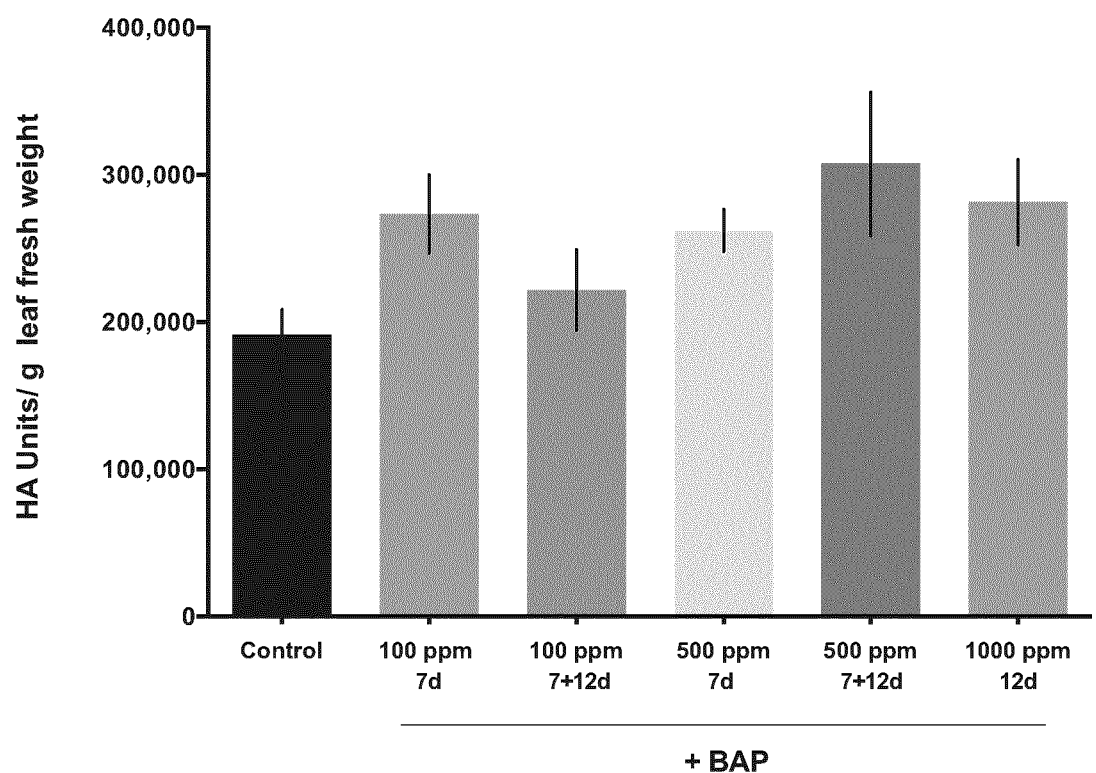
FIG. 10 shows mean rate of HA production (HA units per g fresh weight) in plants treated with 6-benzylaminopurine (BAP) at 100, 500 or 1,000 ppm concentration, 7 and/or 12 days after seedling transplantation.
Figure 11:
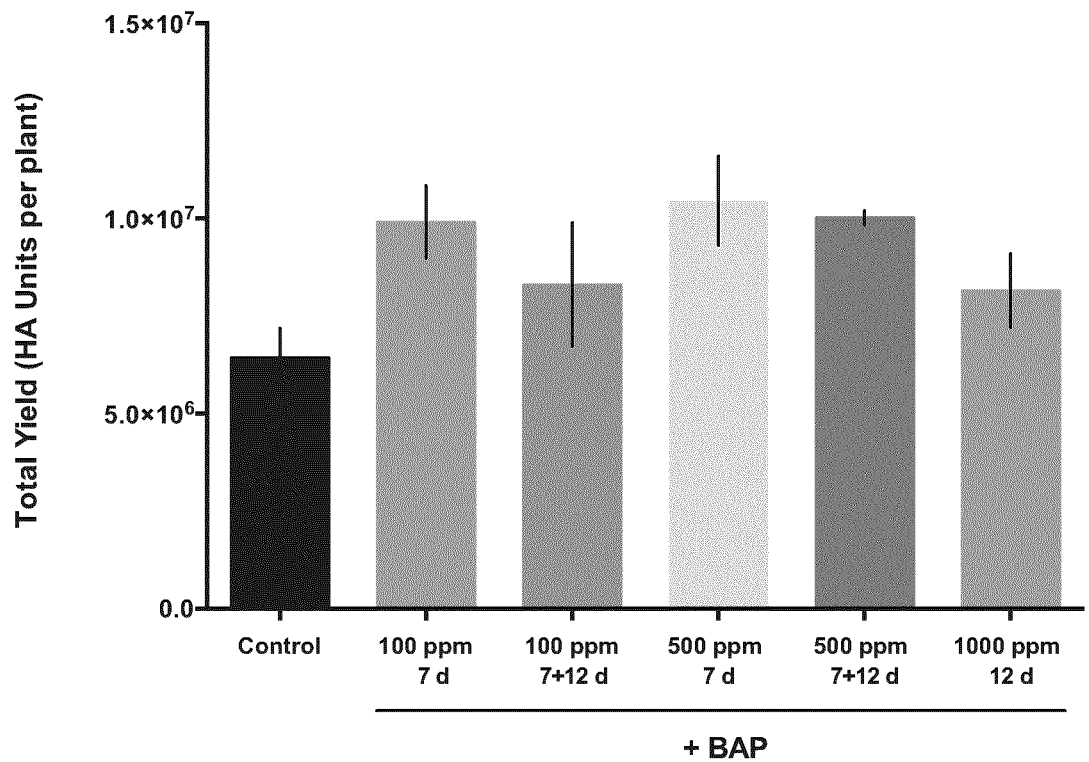
FIG. 11 shows total yield of HA (HA per plant) in plants treated with 6-benzylaminopurine (BAP) at 100, 500 or 1,000 ppm concentration, 7 and/or 12 days after seedling transplantation.

A shown in FIGS. 9, 10 and 11, treatment of plants with BAP had little effect on primary biomass but had a significant positive effect on secondary biomass production (see FIG. 9b).

Furthermore an agent or chemical compound that reduces apical dominance may be applied to the plant, for example the plant may be chemically pruned or otherwise treated to reduce apical dominance. Examples of chemical compounds that may be used include but are not limited to herbicides for example, plant growth regulators Ethephon (e.g. Bromeflor, Cerone, Chlorethephon Ethrel, Florel, Prep and Flordimex), Daminozide (Butanedioic acid mono-2,2-dimethylhydrazine,-Succinic acid 2,2-dimethylhydrazide; e.g. B-nine; Alar, Kylar, SADH, B-nine, B-995, aminozide), Atrimmec (dikegulac sodium), maleic hydrazide (1,2,-dyhydro-3,6-pyridazinedione), and including inhibitors of gibberellic acid synthesis, for example, but not limited to Cycocel (chlormequat chloride), A-Rest (ancymidol), triazols, for example, Bonzi (paclobutrazol), Sumagic (uniconazole), or 3-Amino-1,2,4-triazole (3-AT). These compounds may be used at known dosage ranges for plant growth modification, for example the dosage range used may be those as recommended by the manufacture of the chemical compound. These compounds may be also used at dosage ranges that are below those known for plant growth modification, for example the dosage range used may be used at 75%, 50%, 25%, 10% of that recommended by the manufacture of the chemical compound. These compounds may be used from about 0.2 ppm to about 5,000 ppm, and any amount therebetween, depending upon the growth regulator selected. Furthermore, the pruning agent (chemical compound) may be applied once, or additional applications may be made as required. For example, the chemical compound may be applied one time, or the chemical compound may be applied more than one time, to result in a chemical pruning of the plant prior to, or after infiltration. If chemical pruning is used, then the chemical compound may be applied from about 20 days prior to infiltration to about 2 days after infiltration or any time in between, for example application of a chemical compound at 14 days, 7 days, or 5 days prior to infiltration may effectively be used Pruning of the apical bud may be carried out from about 20 days prior to infiltration, to about 2 days before infiltration or any time in between, for example 19 days prior to infiltration, to about 2 days before infiltration, or any time in between, for example 18 days prior to infiltration, to about 2 days before infiltration, or any time in between, for example 17 days prior to infiltration, to about 2 days before infiltration, or any time in between, for example 16 days prior to infiltration, to about 2 days before infiltration, or any time in between, for example 15 days prior to infiltration, to about 2 days before infiltration, or any time in between, for example 14 days prior to infiltration, to about 2 days before infiltration, or any time in between, for example 15 days prior to infiltration, to about 2 days before infiltration, or any time in between, for example 14 days prior to infiltration, to about 2 days before infiltration, or any time in between, for example 13 days prior to infiltration, to about 2 days before infiltration, or any time in between, for example 12 days prior to infiltration, to about 2 days before infiltration, or any time in between, for example, from about 11 days prior to infiltration to about 2 days prior infiltration, or any time in between, for example, from about 10 days prior to infiltration to about 2 days prior infiltration, or any time in between, for example, from about 9 days prior to infiltration to about 2 days prior infiltration, or any time in between, for example, from about 8 days prior to infiltration to about 2 days prior infiltration, or any time in between, for example, from about 7 days prior to infiltration to about 2 days prior infiltration, or any time in between, for example, from about 6 days prior to infiltration to about 2 days prior infiltration, or any time in between, for example, from about 5 days prior to infiltration to about 2 days prior infiltration, or any time in between, for example, from about 4 days prior to infiltration to about 2 days prior infiltration, or any time in between, for example, from about 3 days prior to infiltration to about 2 days prior infiltration, or any time in between or from 20 days, 19 days, 18, days, 17 days, 16 days, 15 days, 14 days, 13 days, 12 days, 11 days, 10 days, 9 days, 8 days, 7 days, 6 days, 5 days, 4 days 3 days prior to infiltration, to about 2 days prior infiltration, or any time in between. One of skill can readily determine the appropriate interval prior to pruning.

The method may further include harvesting of the plant or a portion of the plant. For example the whole plant comprising primary and secondary stems may be harvested. Alternatively, a portion of the plant comprising secondary biomass, primary biomass, or a combination thereof may be harvested. For example, S1, S2, S3, P1, P2, P3 leaves, S1, S2, S3, P1, P2, P3 leaves with associated petioles, or any combination thereof may be harvested. Old leaves (P3) of the plant may be excluded from harvesting if desired.

By the term "portion of a plant", it is meant any part derived from a plant, including tissue obtained from the plant for example but not limited to the leaves, the leaves and stem, the roots, the aerial portion including the leaves, stem and optionally the floral portion of the plant, cells, protoplasts or any combination thereof obtained from the plant. For example "portion of a plant" may refer to the leaves or stems of a plant. A portion of the plant may also comprise secondary biomass, primary biomass, or a combination thereof, for example, S1, S2, S3, P1, P2, P3 leaves, S1, S2, S3, P1, P2, P3 leaves with associated petioles, or any combination thereof.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

The protein of interest produced according to the present invention may be purified, partially purified from a plant, portion of a plant or plant matter, or may be administered as an oral vaccine, using methods as known to one of skill in the art. Purification may include production of an apoplast fraction as described in WO 2011/035422 (which is incorporated herein by reference). For preparative size exclusion chromatography, a preparation comprising the protein of interest may be obtained and insoluble material removed by centrifugation. Precipitation with PEG may also be used. The recovered protein may be quantified using conventional methods (for example, Bradford Assay, BCA), and the extract passed through a size exclusion column, using for example SEPHACRYL™, SEPHADEX™, or similar medium, and the fractions collected. Blue Dextran 2000 or a suitable protein, may be used as a calibration standard. The extract may also be passed through a cation exchange column and active fractions collected. Following chromatography, fractions may be further analyzed by protein electrophoresis, immunoblot, or both, to confirm the presence of the protein of interest and the protein complement of the fraction.

By the term "minimal processing" it is meant plant matter, for example, a plant or portion thereof comprising a protein of interest which is partially purified to yield a plant extract, homogenate, fraction of plant homogenate or the like (i e minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

By "nucleotide (or nucleic acid) sequence of interest", or "coding region of interest", it is meant any nucleotide sequence, or coding region (these terms may be used interchangeably) that is to be expressed within a host organism, for example a plant, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

The protein of interest may be expressed in any suitable plant host that is transformed by the nucleotide sequence, or constructs, or vectors of the present invention. Examples of suitable hosts include, but are not limited to, *Arabidopsis*, agricultural crops including for example canola, *Brassica* spp., maize, *Nicotiana* spp., (tobacco) for example, *Nicotiana benthamiana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

"Expression cassette" refers to a nucleotide sequence comprising a nucleic acid of interest under the control of, and operably (or operatively) linked to, an appropriate promoter or other regulatory elements for transcription of the nucleic acid of interest in a host cell, for example a plant cell.

By "regulatory region" "regulatory element" or "promoter" it is meant a portion of nucleic acid typically, but not always, upstream of the protein coding region of a gene, which may be comprised of either DNA or RNA, or both DNA and RNA.

By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences. A transcriptional regulatory region and a sequence of interest are operably linked when the sequences are functionally connected so as to permit transcription of the sequence of interest to be mediated or modulated by the transcriptional regulatory region.

When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element.

Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

A constitutive regulatory region directs the expression of a gene throughout the various parts of a plant and continuously throughout plant development. Examples of known constitutive regulatory elements include promoters associated with the CaMV 35S transcript. (Odell et al., 1985, *Nature*, 313: 810-812), the rice actin 1 (Zhang et al, 1991, *Plant Cell*, 3: 1155-1165), actin 2 (An et al, 1996, *Plant J.*, 10: 107-121), or tms 2 (U.S. Pat. No. 5,428,147, which is incorporated herein by reference), and triosephosphate isomerase 1 (Xu et. al., 1994, *Plant Physiol.* 106: 459-467) genes, the maize ubiquitin 1 gene (Cornejo et al, 1993, *Plant Mol. Biol.* 29: 637-646), the *Arabidopsis* ubiquitin 1 and 6 genes (Holtorf et al, 1995, *Plant Mol. Biol.* 29: 637-646), and the tobacco translational initiation factor 4A gene (Mandel et al, 1995 *Plant Mol. Biol.* 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

In another example the protein of interest may be expressed in an expression system that comprises amplification elements and/or regulatory elements or regions (also referred to herein as enhancer elements). For example an amplification element from a geminivirus such as for example, an amplification element from the bean yellow dwarf virus (BeYDV) may be used to express the protein of interest. BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

As used herein, the phrase "amplification elements" refers to a nucleic acid segment comprising at least a portion of one or more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs, may further comprises a short intergenic region (SIR) of a geminivirus genome. As used herein, "short intergenic region" refers to the complementary strand (the short IR (SIR) of a Mastreviruses). Any suitable geminivirus-derived amplification element may be used herein. See, for example, WO2000/20557; WO2010/025285; Zhang X. et al. (2005, *Biotechnology and Bioengineering*, Vol. 93, 271-279), Huang Z. et al. (2009, *Biotechnology and Bioengineering*, Vol. 103, 706-714), Huang Z. et al. (2009, *Biotechnology and Bioengineering*, Vol. 106, 9-17); which are herein incorporated by reference). If more than one LIR is used in the construct, for example two LIRs, then the promoter, CMPV-HT regions and the nucleic acid sequence of interest and the terminator are bracketed by each of the two LIRs.

Enhancer elements may be used to achieve high level of transient expression of the protein of interest. Enhancer elements may be based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology, Recombinant Proteins From Plants*, vol. 483: 25-39), "CPMV HT+" as described in U.S. 61/971,274, which is incorporated herein by reference or "CPMVX" (also referred as "CPMV 160") and/or "CPMVX+" (also referred to as "CPMV 160+") as described in U.S. 61/925,852, which is incorporated herein by reference.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998, *EMBO J.* 17, 6739-6746, which is incorporated herein by reference). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19; the construction of p19 is described in described in WO 2010/0003225, which is incorporated herein by reference), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of *Heracleum* latent virus (HLV-p10), or p16 of Garlic common latent virus (GCLV-p16).

Therefore, one or more suppressors of silencing, for example, but not limited to, HcPro, TEV-p1/HC-Pro, BYV-p21, TBSV p19, TCV-CP, CMV-2b, PVX-p25, rgscam, B2 protein from FHV, the small coat protein of CPMV, and coat protein from TCV, PVM-p11, PVS-p11, BScV-p16, CTV-p23, GLRaV-2 p24, GBV-p14, HLV-p10, GCLV-p16, or GVA-p10 may be co-expressed along with the comovirus-based expression cassette, geminivirus-derived amplification element, and the nucleic acid sequence encoding the protein of interest to further ensure high levels of protein production within a plant.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, Fundamentals of Gene Transfer in Plants. In *Plant Metabolism*, 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100:

247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al., (2987, *Nature* 327: 70-73); Freeman et al. (1984, *Plant Cell Physiol.* 29: 1353), Howell et al. (1980, *Science* 208: 1265), Horsch et al. (1985, *Science* 227: 1229-1231), DeBlock et al., (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth*, 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages 41-50; Liu and Lomonossoff, 2002, *Journal of Virological Methods*, 105:343-348; which is incorporated herein by reference). Alternatively, a vacuum-based transient expression method, as described by Kapila et al., (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al., (Cell Culture and Somatic Cell Genetics of Plants, Vol I, II and III, Laboratory Procedures and Their Applications, Academic Press, 1984), and Weissbach and Weissbach, (Methods for Plant Molecular Biology, Academic Press, 1989). The method of obtaining transformed and regenerated plants is not critical to the present invention.

If plants, plant portion or plant cell are to be transformed or co-transformed by two or more nucleic acid constructs, the nucleic acid construct may be introduced into the *Agrobacterium* in a single transfection event the nucleic acids are pooled, and the bacterial cells transfected as described. Alternately, the constructs may be introduced serially. In this case, a first construct is introduced to the *Agrobacterium* as described, the cells grown under selective conditions (e.g. in the presence of an antibiotic) where only the singly transformed bacteria can grow. Following this first selection step, a second nucleic acid construct is introduced to the *Agrobacterium* as described, and the cells grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, a plant portion, or a plant cell are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

The protein of interest may comprise a native, or a non-native signal peptide; the non-native signal peptide may be of plant origin. For example, the signal peptide may be a protein disulfide isomerase signal peptide (PDI). The native signal peptide may correspond to that of the protein of interest being expressed. The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to one or more proteins from Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood dotting factors, for example, Factor VIII, Factor IX, or tPA hGH, receptors, receptor agonists, antibodies for example but not limited to Rituxan, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may also include an influenza hemagglutinin (HA; see WO 2009/009876, which is incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008 Nucleic Acids Research 36:D497-D503) at URL: biohealthbase.org/GSearch/home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, and H16. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

The HA protein may be an H1, H2, H3, H5, H6, H7 or H9 subtype. For example, the H1 protein may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein may also be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/HongKong/W312/97 (H6N1) strain. The H7 protein may be from the A/Equine/Prague/56 (H7N7) strain, or H7 A/Hangzhou/1/2013, A/Anhui/1/2013 (H7N9), or A/Shanghai/2/2013 (H7N9) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The HA may comprise a native, or a non-native signal peptide; the non-native signal peptide may be of plant origin. For example, the signal peptide may be a protein disulfide isomerase signal peptide (PDI). The native signal peptide may correspond to that of the hemagglutinin being expressed, or may correspond to a second hemagglutinin.

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15, H16 or HA from type B influenza. For example, the HA protein encoded by the nucleic acid molecule may be an H1, H2, H3, H5, H6, H7, H9 subtype an HA from type B. The H1 protein encoded by the nucleic acid may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein encoded by the nucleic acid molecule may be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. The H2 protein encoded by the nucleic acid molecule may be from the A/Singapore/1/57 (H2N2) strain. The H5 protein encoded by the nucleic acid molecule A/Anhui/1/2005 (H5N1), A/Vietnam/1194/2004 (H5N1), or A/Indonesia/5/2005 strain. The H6 protein encoded by the nucleic acid molecule may be from the A/Teal/HongKong/W312/97 (H6N1) strain. The H7 protein encoded by the nucleic acid molecule may be from the A/Equine/Prague/56 (H7N7) strain, or H7 A/Hangzhou/1/2013, A/Anhui/1/2013 (H7N9), or A/Shanghai/2/2013 (H7N9) strain. Additional, the H9 protein encoded by the nucleic acid molecule may be from the A/HongKong/1073/99 (H9N2) strain. The HA protein encoded by the nucleic acid molecule may be from an influenza virus type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

It is contemplated that a plant comprising the protein of interest may be administered to a subject, for example an animal or human, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible.

TABLE 1

Listing of sequences:

| SEQ ID NO: | Description |
|---|---|
| 1 | Primer IF-PDI.S1 + 3c |
| 2 | Primer IF-H1cTMCT.S1-4r |
| 3 | Nucleotide sequence of PDISP/H1 California. |
| 4 | Nucleotide sequence of construct 1191 (FIG. 15) |
| 5 | Nucleotide sequence of cassette 484 PDISP/H1 Calf (FIG. 16) |
| 6 | Amino acid sequence of PDISP/H1 Calf |

EXAMPLES

Example 1: A-2X35S/CPMV-HT/PDISP/H1 California/NOS (Construct Number 484)

Figure 7:
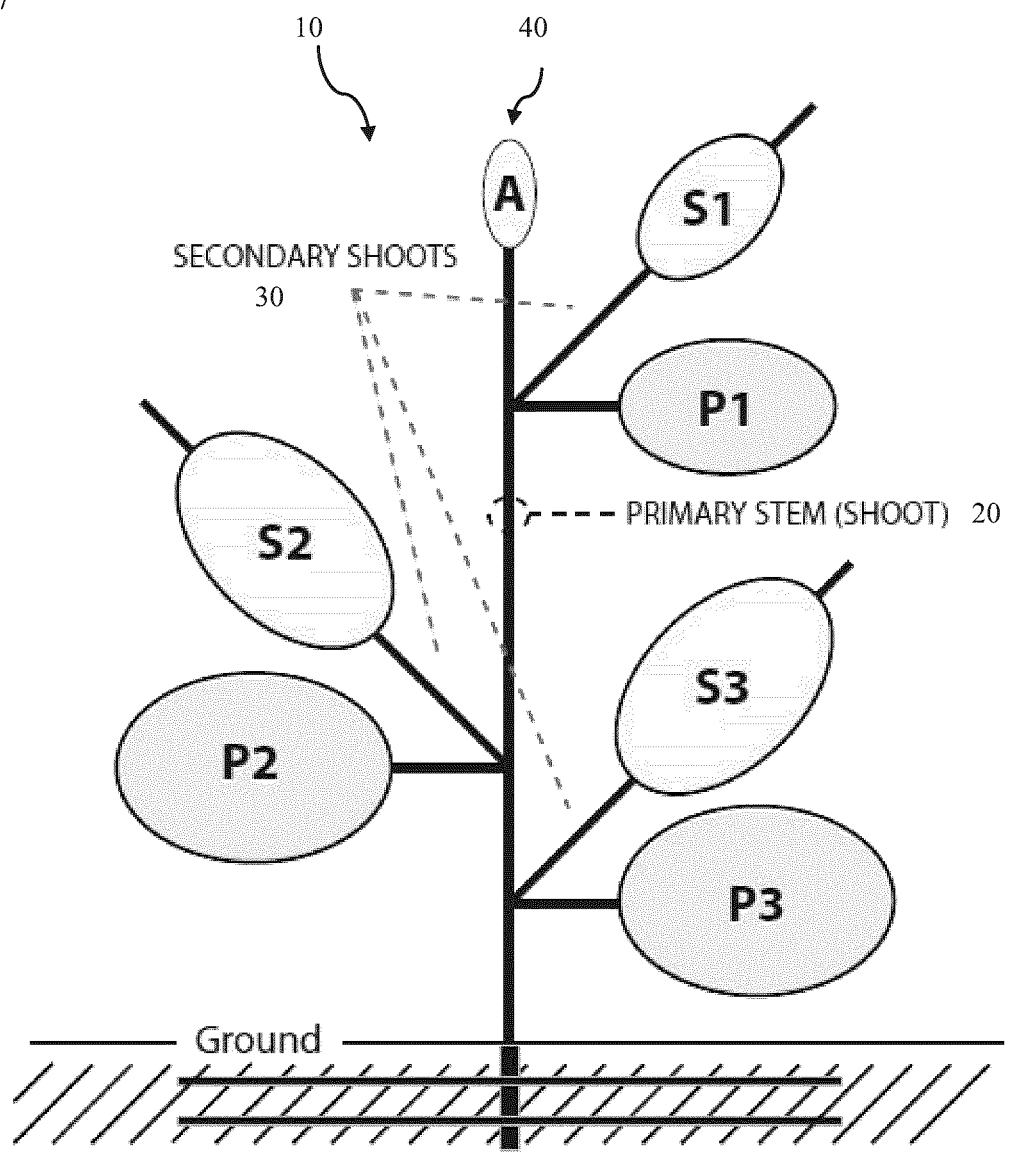
FIG. 7 shows a schematic diagram of a plant with primary (P1, P2, P3) and secondary leaves (S1, S2, S3).

A sequence encoding H1 from Influenza A/California/7/2009 in which the native signal peptide has been replaced by that of alfalfa protein disulfide isomerase (PDISP/H1 California) was cloned into 2X35S-CPMV-HT-NOS expression cassette using the following PCR-based method. A fragment containing the PDISP/H1 California coding sequence was amplified using primers IF-PDI.S1+3c (FIG. 12A, SEQ ID NO: 1) and IF-H1cTMCT.S1-4r (FIG. 12B, SEQ ID NO: 2), using PDISP/H1 California sequence (FIG. 13, SEQ ID NO:3) as template. The PCR product was cloned in 2X35S/CPMV-HT/NOS expression system using In-Fusion cloning system (Clontech, Mountain View, CA). Construct number 1191 (FIG. 14) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 15 (SEQ ID NO: 4). The resulting construct was given number 484 (FIG. 16, SEQ ID NO: 5). The amino acid sequence of mature H1 from Influenza A/California/7/2009 fused with PDISP is presented in FIG. 17 (SEQ ID NO: 6). A representation of plasmid 484 is presented in FIG. 18.

Example 2: *Agrobacterium* Transfection

*Agrobacterium* strain AGL1 was transfected by electroporation with the DNA constructs using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an OD600 between 0.6 and 1.6. *Agrobacterium* suspensions were centrifuged before use and resuspended in infiltration medium (10 mM MgCl2 and 10 mM MES pH 5.6).

Preparation of Plant Biomass, Inoculum and Agroinfiltration

*Nicotiana benthamiana* plants were grown from seeds in flats filled with a commercial peat moss substrate. The plants were allowed to grow in the greenhouse under a 16/8 photoperiod and a temperature regime of 28° C. day/24° C. night. Three weeks after seeding, individual plantlets were picked out, transplanted in pots and left to grow in the greenhouse for three additional weeks under the same environmental conditions.

Agrobacteria transfected with each construct were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an OD600 between 0.6 and 1.6. *Agrobacterium* suspensions were centrifuged before use and resuspended in infiltration medium (10 mM MgCl2 and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Infiltrated plants were put in a PGR15 CMP 5090 Conviron chamber (Conviron, Winnipeg MB, Canada) for a 6-7 day incubation period until harvest.

Example 3: Analytical Procedures

Leaf proteins were extracted from primary, P1, P2, P3 leaves and petioles and secondary, S1, S2, S3 leaves and petioles, based on the scheme provided in FIG. 7. Harvested leaves were weighed to determine biomass production on a fresh leaf tissue basis. Leaf proteins were extracted in 50 mM Tris-HCl, pH 8.0, containing 500 mM NaCl, 1 mM PMSF and 0.04% (w/v) sodium metabisulfite (extraction buffer), using an Omni bead Ruptor 24 homogenizer and 2.8-mm zirconium beads (OMNI International, Kennesaw GA, U.S.A.) for leaf tissue disruption. Harvested leaf tissue was frozen at −80° C. and ground in liquid nitrogen, diluted in extraction buffer (1.5 g fresh leaf powder in 3 mL of extraction buffer containing 10 zirconium beads), and homogenized in the Omni bead Ruptor homogenizer according to the supplier's instructions. One mL of mixture was transferred in a 1.5-mL microtube and centrifuged at 20,000 g for 10 min at 4° C., and the supernatant recovered for further analysis. Protein content in the supernatant was determined according to Bradford (Bradford MM (1976) Analytical Biochemistry 72, 248-254), with bovine serum albumin as a protein standard. The samples were kept on ice or frozen at −80° C. prior to hemagglutination assay.

Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, NY; for all B strains, H1, H5 and H7) or 0.5% guinea pig red blood cells suspension (for H3) were added to each well, and plates were incubated for 2 h at room temperature. The reciprocal of the highest dilution showing complete hemagglutination was recorded as HA activity.

Leaf RNA was extracted from primary, P1, P2, P3 leaves and petioles and secondary, 51, S2, S3 leaves and petioles, based on the scheme provided in FIG. 7. mRNA transcripts the HA coding sequence were assayed by real-time RT PCR using an ABI PRISM 7500 Fast real-time PCR apparatus, system version 2.0.1 (Applied Biosystems). Total RNA was extracted as described earlier by Robert et al. (PLoS One, 8: e70203) using the Qiagen RNeasy plant mini kit (Qiagen), following the supplier's instructions. RNA samples were treated with DNase I (Roche Diagnostics) to remove contaminant DNA and assessed for quality and quantity using a Nanodrop® ND-1000 spectrophotometer (NanoDrop Technologies, Wilmington DE, USA). First-strand cDNA was synthesized from 500 ng of total RNA using 4 units of Omniscript reverse transcriptase (Qiagen) and 1 µM of oligo-dT(15) nucleotides (Roche). PCR mixtures contained 10 µl of Fast SYBR Green PCR Master Mix (Applied Biosystems), 2 µl of cDNA template, and 2.5 µl each of appropriate forward and reverse primers at 625 nM final concentration. A no-template mixture control was included in each 96-well plate Amplification rounds consisted of a 20-s denaturation step at 95° C., followed by 40 two-step cycles of 3 s at 95° C. and 30 s at 60° C. A dissociation curve analysis was performed after amplification with the SYBR Green Master Mix, and the cycle threshold of each sample was then compared to a DNA standard curve designed for each pair of primers. Standard curves were generated with 2 µl of cDNA template following the NEB Taq polymerase routine protocol (New England Biolabs) Amplification products were purified using the Illustra GFX kit (GE Healthcare) and DNA standard curves were devised with serial dilutions of the purified PCR products in nuclease free-water (from 107 to 102 copies per µl). Ct data were plotted against the corresponding number of transcript copies. All amplifications were carried out in duplicate.

Example 4: Lighting Assays

Figure 5:
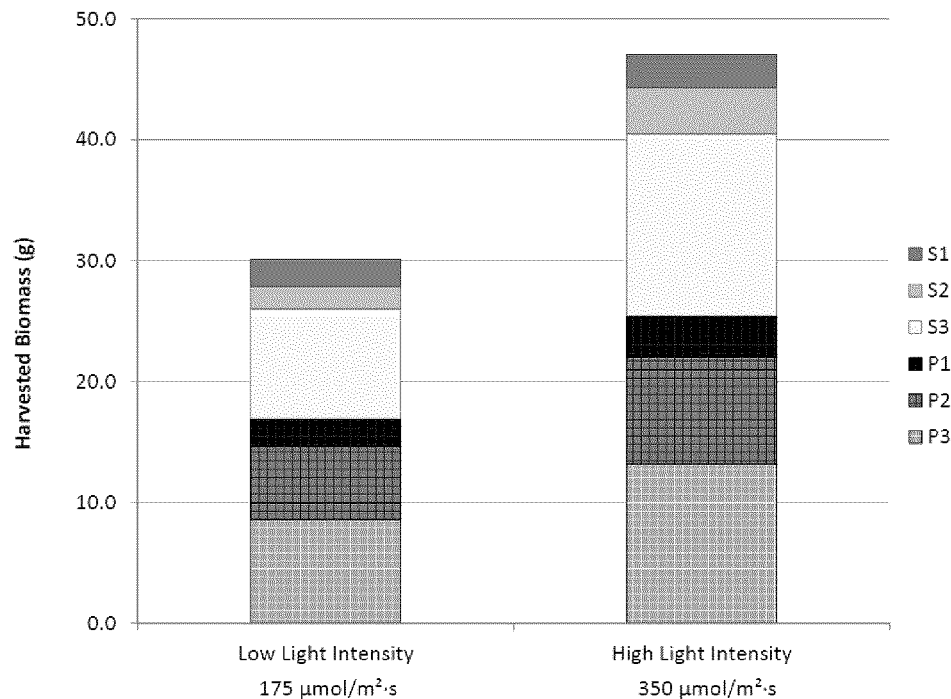
FIG. 5 shows the biomass production of plants grown in a growth chamber either in low light or high light intensity. Young (P1), mature (P2) and old (P3) leaves of the main stem and young (S1), mature (S2) and old (S3) leaves of secondary stems were harvested and the biomass was determined.
Figure 6:
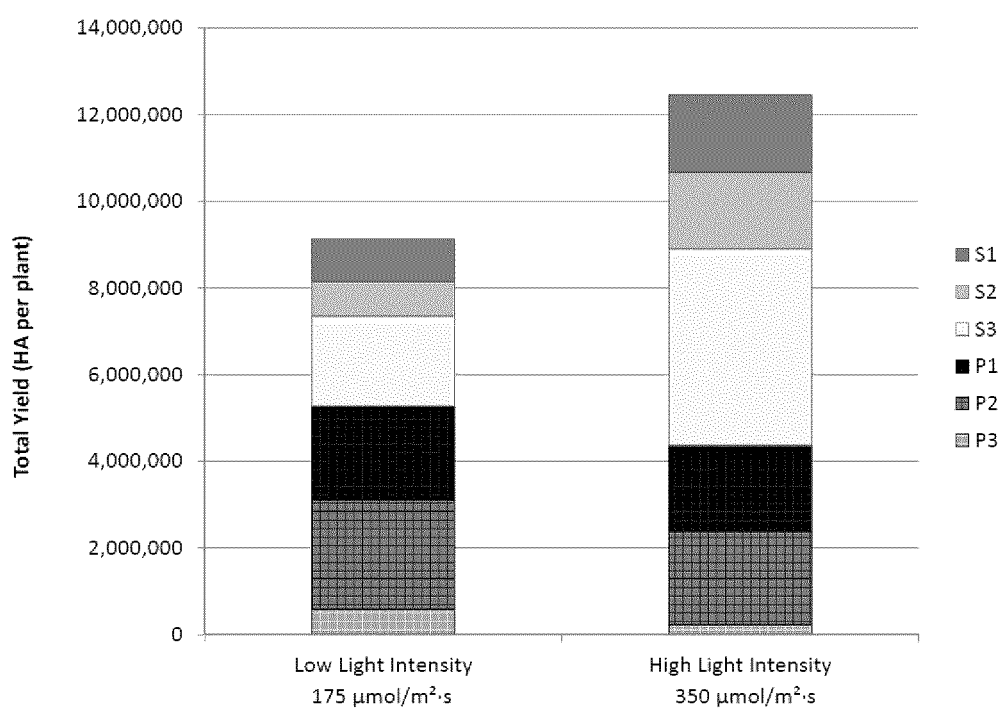
FIG. 6 shows the total yield of HA per plant grown in a growth chamber either in low light or high light intensity. Young (P1), mature (P2) and old (P3) leaves of the main stem and young (S1), mature (S2) and old (S3) leaves of secondary stems were harvested and the total yield of HA per plant was determined.

Different lighting regimes were used for biomass production prior to agroinfiltration, using standard growth chamber conditions (as defined in Example 2, above) as a baseline comparator. Three week-old seedlings were transplanted in pots as described in Example 2, above, and left to produce biomass for three weeks in greenhouse (FIGS. 1-4) or in Conviron PGW36 3224 growth chambers (FIGS. 5 and 6). The plants were then agroinfiltrated with an *Agrobacterium* strain transformed with construct 484 for the exapression of H1 from Influenza A/California/7/2009 (HA; Example 1), left to express the protein of interest (HA) for 6-7 days and assessed for biomass and HA production as described in Examples 2 and 3. Light treatments in greenhouse and growth chamber trials involved different lighting devices, including 1,000 W high pressure sodium (HPS) lamps (Philips), 1,000 W metal halide (MH) lamps (Sylvania) and GreenPower LED lamps (Phillips)

For the greenhouse trials, the following lighting regimes were used:
 (1) 16 h day/8 h night photoperiod, light intensity of 80 µmol/m$^2$·s;
 (2) 16 h day/8 h night photoperiod, light intensity of 160 µmol/m$^2$·s;
 (3) 24 h day photoperiod, light intensity of 80 µmol/m$^2$·s;
 (4) 24 h day photoperiod, light intensity of 160 µmol/m$^2$·s.

For the growth chamber trials, the following lighting regimes were used:
 (1) 24 h day photoperiod, light intensity of 175 µmol/m$^2$·s (low light intensity control);
 (2) 24 h day photoperiod, light intensity of 350 µmol/m$^2$·s (high light intensity trial).

Results of the trials are shown in FIGS. 1-6.

Regarding the greenhouse trials (FIG. 1-4), with an increase in light intensity (from 80 to 160 µmol/m$^2$·s), a corresponding increase is total leaf biomass was observed for plants that were exposed to a 16 hr or a 24 hr photoperiod (FIG. 1). Furthermore, the proportion of secondary leaf biomass to primary leaf biomass increased along with the increase in the photoperiod and with the increase in the light intensity from a secondary leaf biomass to primary leaf biomass ratio (S/P) of: S/P ratio of 0.27:1 for the 16 h 80 treatment, S/P ratio of 0.39:1 for the 16 h 160 treatment; S/P ration of 0.44:1 for 24 h 80 treatment, and S/P ratio of 0.53:1 for the 24 h 160 treatment. Demonstrating an increase in the amount of secondary leaf biomass resulting from these two light treatments (increased light intensity and increased photoperiod).

Figure 2:
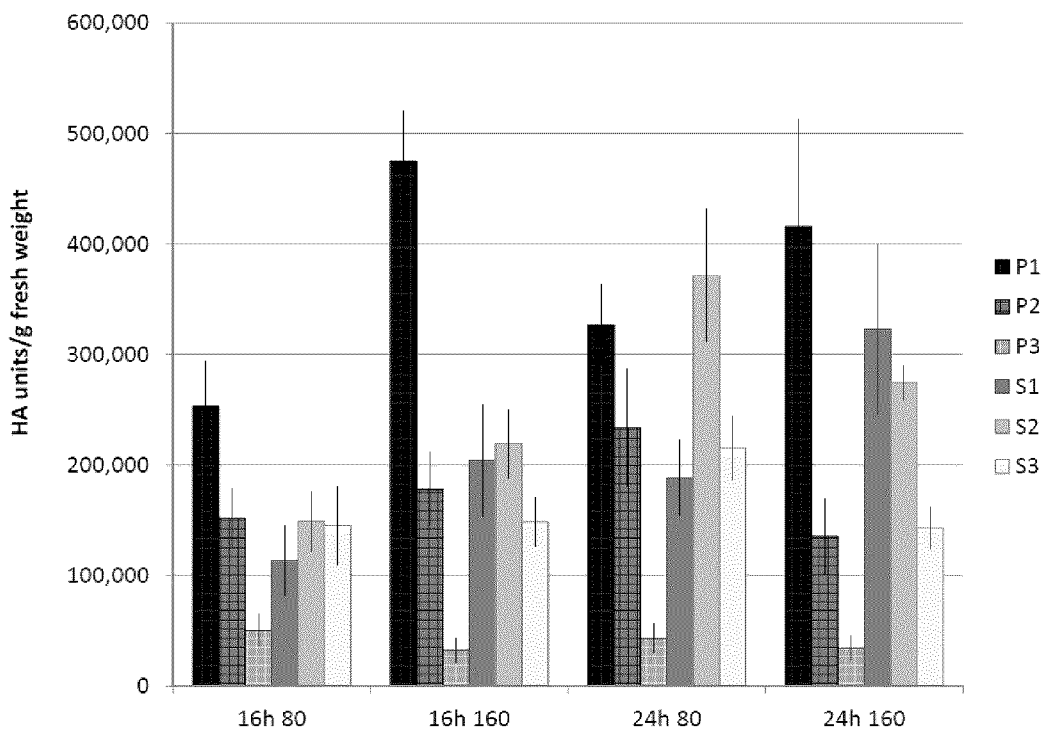
FIG. 2 shows HA production in young (P1), mature (P2) and old (P3) leaves of the main stem and young (S1), mature (S2) and old (S3) leaves of secondary stems under different light photoperiods (16 h and 24 h) and light intensity treatments (80 and 160 µmol/m2·s).
Figure 3:
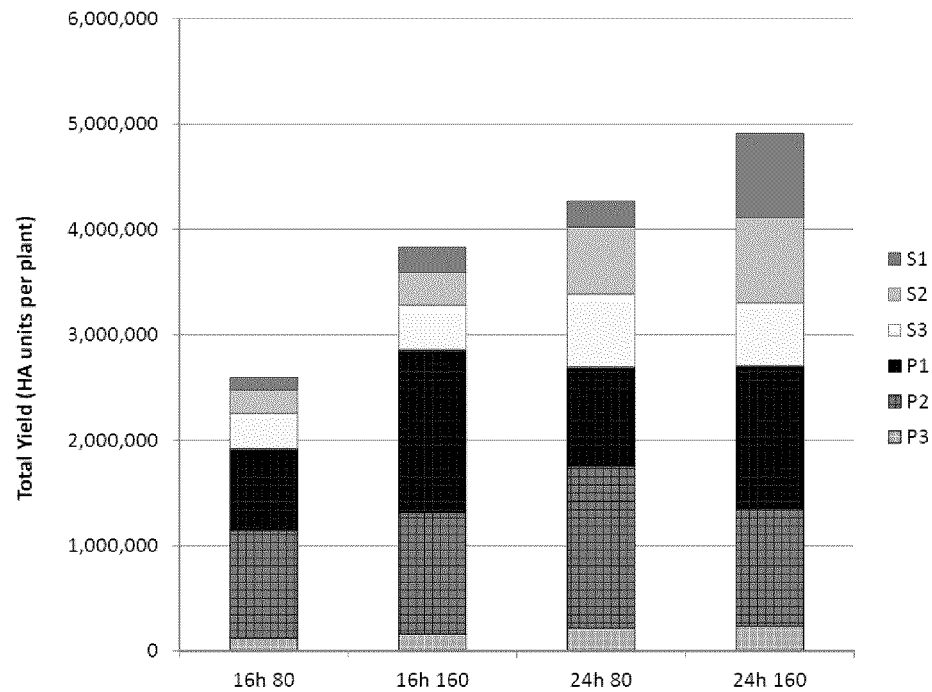
FIG. 3 shows total yield of HA (HA per plant) in young (P1), mature (P2) and old (P3) leaves of the main stem and young (S1), mature (S2) and old (S3) leaves of secondary stems under different light photoperiods (16 h and 24 h) and light intensity treatments (80 and 160 µmol/m2·s).
Figure 4:
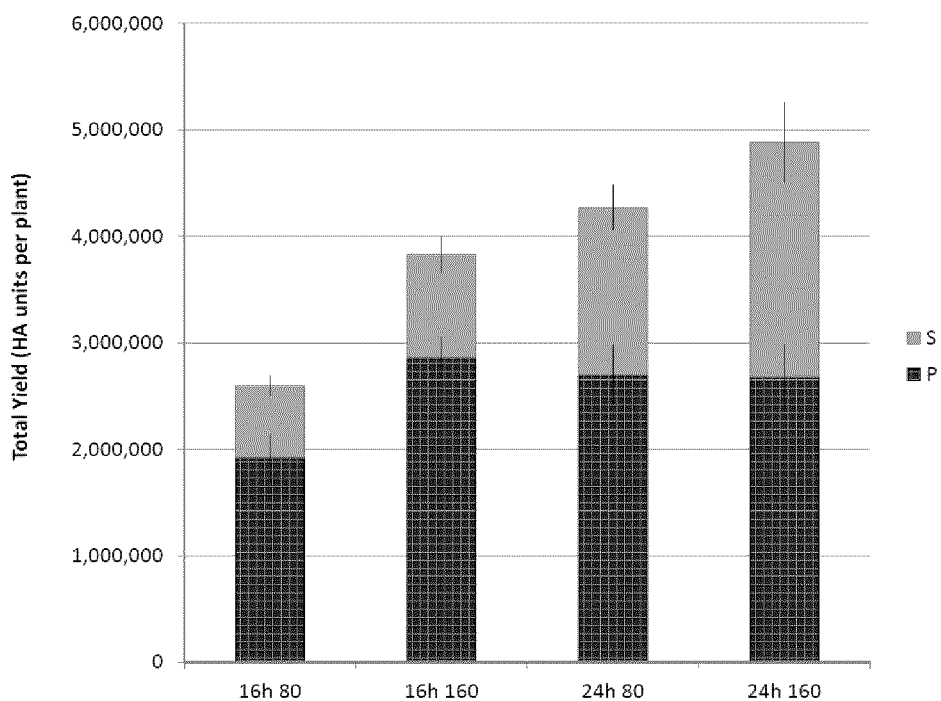
FIG. 4 shows total yield of HA in leaves of the main stem (bottom (P)) and the leaves of secondary stems (top (S)) under different light photoperiods (16 h and 24 h) and light intensity treatments (80 and 160 µmol/m2·s).

The yield of the protein of interest (HA) also increase in the secondary leaf biomass as a result of the light intensity and photoperiod treatments (FIGS. 2, 3 and 4). Furthermore, the ratio of HA protein yield obtained from secondary leaf biomass to primary leaf biomass (HA S/P ratio) increased from HA S/P ratio of 0.33:1 for the 16 h 80 treatment, HA S/P ratio of 0.35:1 for the 16 h 160 treatment; HA S/P ration of 0.62:1 for 24 h 80 treatment, and HA S/P ratio of 0.89:1 for the 24 h 160 treatment. Demonstrating an increase in the protein of interest yield in secondary leaf biomass resulting from these two light treatments (increased light intensity and increased photoperiod). The yield of a protein of interest from the total leaf biomass (primary and secondary) increased with increased light intensity and increased photoperiod (FIGS. 3 and 4).

Similar results were obtained with the growth chamber trials (FIGS. 5 and 6, and Table 2). As shown in FIG. 5, with an increase in light intensity, there was a corresponding increase in total leaf biomass. An increase in the yield of HA obtained from secondary leaf biomass when compared to the yield of HA obtained from primary leaf biomass was also observed (FIG. 6). This was associated with a higher number of mRNA transcripts for HA biosynthesis in oldest secondary leaves (S3) compared to corresponding number in oldest primary leaves (P3) (Table 2).

These data collectively demonstrate that by increasing the growth of secondary leaf biomass prior to infiltration and harvest result in an increase in the secondary leaf biomass is obtained, along with an increase in the biosynthetic rate and yield of a protein of interest. It is to be understood that the protein of interest may be obtained from the second leaf biomass, the primary leaf biomass, or both the secondary leaf biomass and the primary leaf biomass.

TABLE 2 mRNA transcripts for HA in young (P1), mature (P2) and old (P3) leaves of the main stem, and in young (S1), mature (S2) and old (S3) leaves of secondary stems, of growth chamber-cultivated plants.

| Production Unit | HA transcripts (Millions of copies/mg leaf f.w.) |
| --- | --- |
| P1 | 4.57 ± 1.68 a |
| S1 | 3.95 ± 1.43 a |
| P2 | 3.20 ± 0.84 ab |
| S2 | 3.39 ± 1.35 b |
| S3 | 1.96 ± 0.77 c |
| P3 | 0.47 ± 0.22 d |

Example 5: Physical Pinching Treatments after Seedling Transplantation

The relative importance of secondary shoots over total harvested biomass was boosted by removing the apical (main stem) bud 40 (see 'A', on FIG. 7) 5, 7 or 12 days after seedling transplantation, corresponding, respectively, to 16, 14 or 9 days prior to infiltration. Three week-old seedlings were transplanted in pots, left to produce biomass for one week in greenhouse, and the apex removed to produced pruned plants. The pruned plants were left in the greenhouse for a further 16, 14 or 9 days. The pruned plants were then agroinfiltrated with an *Agrobacterium* strain transformed with construct 484 for the exapression of H1 from Influenza A/California/7/2009 (HA; Example 1)) as described in Example 2, and placed in a PGR15 CMP 5090 Conviron chamber (under conditions defined in Example 2), and left of for 6-7 days. After this period of time the pruned plants were assessed for biomass as described in Example 3. After this period of time the pruned plants were assessed for biomass and HA production as described in Example 3. The following conditions were used for the trial: a 24 h day/0 h night photoperiod, a light intensity of 160 µmol/m$^2$·s provided by HPS (Philips) and MH (Sylvania) lamps, a temperature regime of 28° C. day/24° C. night, and a plant canopy density of 33 plants/m$^2$.

Figure 8:
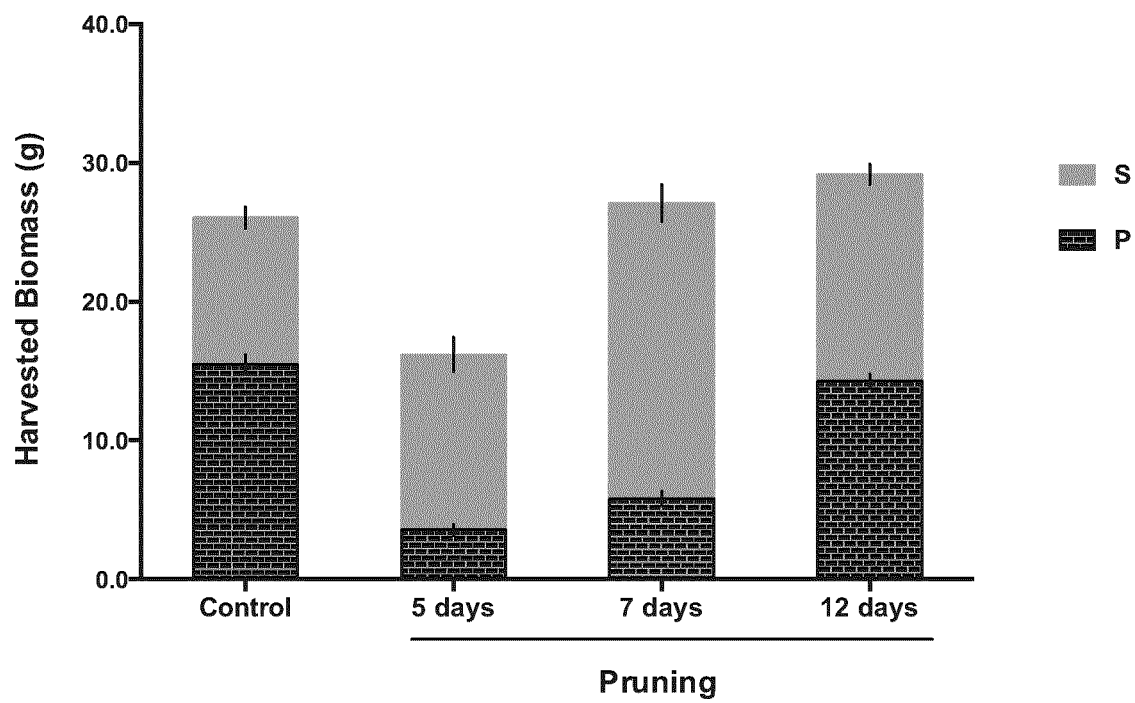
FIG. 8 shows the effect of pruning, in this case the removal of the apical bud from plants 5, 7 or 12 days after seedling transplantation, on total primary biomass (P) versus total secondary biomass (S) per plant.

Results of pruning the apical bud prior to plant transformation on plant biomass are presented in Table 3 and FIG. 8. Pruning did not alter the total leaf biomass (i.e. primary and second leaf biomass combined), except for early pinching 5 days after transplantation significantly affecting plant growth (FIG. 8). As a result of pruning, the proportion of the leaf biomass shifted with secondary leaf biomass (see FIG. 8 for biomass harvested following HA incubation). For instance, secondary leaf biomass as determined prior infiltration increased from 10.4 g in control plants (not pruned) to 23.0 g in pruned plants, while the primary leaf biomass decreased from 26.3 g (control) to 14.5 g (pruned plants), for a ratio of secondary leaf biomass to primary leaf biomass increasing from 0.4:1 to 1.6:1.

These data collectively demonstrate that mechanical pinching after seedling transplantation is a way to increase the relative importance of secondary leaf biomass at the whole plant scale, prior to infiltration for improved production of a protein of interest. It is to be understood that the protein of interest may be obtained from the second leaf biomass, the primary leaf biomass, or both the secondary leaf biomass and the primary leaf biomass.

TABLE 3

Effect of pruning 7 days after seedling transplantation on primary leaf biomass, secondary leaf biomass and total leaf biomass (g fresh weight).

|  | Average Total leaf biomass | Average Primary leaf biomass | Average Secondary leaf biomass |
|---|---|---|---|
| Control plants | 36.7 ± 4.0 | 26.3 ± 2.5 | 10.4 ± 1.9 |
| Pruned plants | 37.5 ± 6.0 | 14.5 ± 4.6 | 23.0 ± 3.4 |

Example 6: Chemical Treatments with the Synthetic Hormone Benzylaminopurine (BAP) after Seedling Transplantation The relative importance of secondary shoots over total harvested biomass was boosted by treating the plants with the synthetic plant hormone benzylaminopurine (BAP) 7 or 12 days after seedling transplantation, i.e. 14 or 9 days prior to infiltration for HA expression. Three week-old seedlings were transplanted in pots, left to produce biomass for 7 or 12 days in greenhouse, and treated after 7 and/or 12 days with the synthetic hormone at working doses of 100 ppm, 500 ppm or 1,000 ppm in water. The treated plants were left in the greenhouse for a further 14 or 9 days, and then agroinfiltrated with an *Agrobacterium* strain transformed with construct 484 for the exapression of H1 from Influenza A/California/7/2009 (HA; Example 1)) as described in Example 2, and placed in a PGR15 CMP 5090 Conviron chamber (under conditions defined in Example 2), and left of for 6-7 days. After this period of time the treated plants were assessed for biomass and HA production as described in Example 3. The following conditions were used for the trial: a 24 h day/0 h night photoperiod, a light intensity of 160 µmol/m$^2$·s provided by HPS (Philips) and MH (Sylvania) lamps, a temperature regime of 28° C. day/24° C. night, and a plant canopy density of 33 plants/m$^2$.

Results of treating plants with BAP prior to plant transformation on plant biomass and HA yield are presented in FIGS. 9, 10 and 11. BAP treatment had little effect on primary biomass but had a significant positive effect on secondary biomass production, except for the 1,000 ppm treatment showing no positive impact (FIG. 9). For instance, ca. 22 g of secondary leaf biomass was harvested from plants treated with 500 ppm 7 days after transplantation compared to ca. 16 g for control (non-treated) plants, for a relative increase of about 37.5% compared to a less than 10% increase for primary biomass.

The increased proportion of secondary biomass in BAP-treated plants was associated with an overall, consolidated increase of HA production per g fresh weight (FIG. 10) and a consequent increase of HA total yield per plant (FIG. 11). For instance, the yield of HA per g fresh weight in control (non-treated) plants was less than 200,000 units compared to more than 300,000 units per g fresh weight in plants treated with BAP at 500 ppm after 7 and 12 days (FIG. 10), for a total yield per plant increased by 45-50%.

These data collectively demonstrate the effectiveness of post-seedling transplantation treatments with the synthetic cytokinin BAP to increase the relative importance of secondary leaf biomass at the whole plant scale prior to infiltration, and to improve the production of a protein of interest post-infiltration. It is to be understood that the protein of interest may be obtained from the second leaf biomass, the primary leaf biomass, or both the secondary leaf biomass and the primary leaf biomass.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method for increasing yield of a heterologous protein in a *Nicotiana* plant per gram fresh leaf weight and per plant, the heterologous protein of interest comprising an influenza hemagglutinin (HA) protein, the method comprising:
   a) treating the plant to increase secondary leaf biomass, wherein the treating comprises cultivating the plant in the presence of 100 to 700 ppm of a cytokinin under growth conditions of 12 hours to 24 hours light per day and a light intensity of 60 µmol/m$^2$·s to 350 µmol/m$^2$·s to produce a treated plant;
   b) introducing one or more than one nucleic acid into the treated plant, the nucleic acid comprising a nucleotide sequence encoding the hemagglutinin (HA) protein, the nucleotide sequence operatively linked to a regulatory region that is active in the plant;
   c) incubating the treated plant under conditions that permit the expression of the nucleotide sequence encoding the hemagglutinin (HA) protein, thereby increasing yield of the hemagglutinin (HA) protein per gram fresh leaf weight and per plant compared with the yield of the hemagglutinin (HA) protein obtained from the same plant tissue of a similar plant that is grown under the same conditions, but that has not been treated to increase the secondary leaf biomass; and followed by
   d) harvesting one or more of S3 leaves S2 leaves and S1 leaves from the treated plant;
wherein the step of treating, step a), is performed from 40 days prior to the step of introducing, step b), up to 9 days prior to the step of introducing, step b).

2. The method of claim 1, wherein in the step of treating, step a), the treated plant has a ratio of secondary leaf biomass to primary leaf biomass between 0.2:1 and 1:1.

3. The method of claim 1, further comprising a step (e) of purifying the hemagglutinin (HA) protein.

4. The method of claim 1, wherein the expression of the nucleotide sequence encoding the HA protein in step c) is transient.

5. The method of claim 1, wherein the expression of the nucleotide sequence encoding the HA protein in step c) is stable.

6. The method of claim 1, wherein the influenza HA proteins assemble into virus like particle (VLP).

7. The method of claim 1, wherein the increase in secondary leaf biomass is a result of an increase in the number of secondary stems and leaves, an increase in the length of secondary stems and leaves, or both.

8. The method of claim 1, wherein the cytokinin is a synthetic cytokinin.

9. The method of claim 8, wherein the synthetic cytokinin is 6 benzylaminopurine (BAP).

10. The method of claim 1, wherein the step of treating the plant, step a), is carried out from 20 days prior to the step of introducing the nucleic acid, step b), up to 9 days prior to the day of introducing the nucleic acid, step b).

11. The method of claim 1, wherein the plant is cultivated in the presence of the cytokinin 9 days prior, 10 days prior, 11 days prior, 12 days prior, 13 days prior, or 14 days prior to the step of introducing, step b).

12. The method of claim 1, wherein step a) further comprises exposing the plant to light duration during growth of the plant for 17 hours to 24 hours per day.

13. The method of claim 1, wherein step a) further comprises exposing the plant to a light intensity during growth of the plant of 90 µmol/m$^2$·s to 350 µmol/m$^2$·s.

14. The method of claim 1, wherein the treating in step a) consists of treating leaves, stems, flowers, or a combination thereof.

15. The method of claim 1, wherein the plant is *Nicotiana benthamiana*.

16. A method of using 6-benzylaminopurine (BAP) to increase yield of a heterologous protein of interest in a *Nicotiana* plant per gram fresh leaf weight and per plant, the heterologous protein of interest comprising an influenza hemagglutinin (HA) protein, the method comprising:
   a) cultivating the *Nicotiana* plant in the presence of 100 to 700 ppm of the BAP under growth conditions of 12 hours to 24 hours light per day and a light intensity of 60 μmol/m²·s to 350 μmol/m²·s to produce a treated plant;
   b) introducing one or more than one nucleic acid into the treated plant, the nucleic acid comprising a nucleotide sequence encoding the hemagglutinin (HA) protein, the nucleotide sequence operatively linked to a regulatory region that is active in the plant;
   c) incubating the treated plant under conditions that permit the expression of the nucleotide sequence encoding the HA protein, wherein the yield of the HA protein per gram fresh leaf weight and per plant is increased when compared with the yield of the HA protein obtained from the same plant tissue of a similar plant that is grown under the same conditions, but that has not been cultivated in the presence of 100 to 700 ppm of the BAP; and followed by
   d) harvesting one or more of S3 leaves S2 leaves and S1 leaves from the treated plant;
wherein the step of treating, step a), is performed from 40 days prior to the step of introducing, step b), up to 9 days prior to the step of introducing, step b).

17. The method of claim 1, wherein the step of harvesting, step d), further comprises harvesting P2 leaves, P1 leaves, or P2 leaves and P1 leaves.

18. The method of claim 16, wherein the step of harvesting, step d), further comprises harvesting P2 leaves, P1 leaves, or P2 leaves and P1 leaves.

\* \* \* \* \*